US008421445B2

(12) United States Patent
Iida

(10) Patent No.: US 8,421,445 B2
(45) Date of Patent: Apr. 16, 2013

(54) POSITION DETECTING SYSTEM AND POSITION DETECTING METHOD

(75) Inventor: Takahiro Iida, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 45 days.

(21) Appl. No.: 13/209,720

(22) Filed: Aug. 15, 2011

(65) Prior Publication Data

US 2012/0098523 A1 Apr. 26, 2012

Related U.S. Application Data

(63) Continuation of application No. PCT/JP2011/050402, filed on Jan. 13, 2011.

(30) Foreign Application Priority Data

Feb. 18, 2010 (JP) ................................ 2010-033664

(51) Int. Cl.
*G01R 35/00* (2006.01)
*G01B 7/14* (2006.01)

(52) U.S. Cl.
USPC ..................................... 324/202; 324/207.15

(58) Field of Classification Search .................. 324/202, 324/207.15
See application file for complete search history.

(56) References Cited

U.S. PATENT DOCUMENTS

| 2008/0306340 | A1* | 12/2008 | Uchiyama et al. ............. 600/117 |
| 2009/0093678 | A1  | 4/2009  | Kimura et al. |
| 2009/0237073 | A1  | 9/2009  | Uchiyama et al. |
| 2009/0295386 | A1* | 12/2009 | Sato et al. ..................... 324/309 |
| 2010/0060472 | A1  | 3/2010  | Kimura et al. |
| 2010/0179782 | A1  | 7/2010  | Kimura et al. |
| 2010/0204566 | A1  | 8/2010  | Uchiyama et al. |
| 2010/0219825 | A1  | 9/2010  | Sato et al. |

FOREIGN PATENT DOCUMENTS

| JP | 2006-271520 A | 10/2006 |
| JP | 2007-175317 A | 7/2007 |
| JP | 2008-079913 A | 4/2008 |
| JP | 2009-039356 A | 2/2009 |
| JP | 2009-226080 A | 10/2009 |

(Continued)

OTHER PUBLICATIONS

International Search Report dated Mar. 1, 2011 from corresponding International Application No. PCT/JP2011/050402 together with English language translation.

*Primary Examiner* — Bot Ledynh
(74) *Attorney, Agent, or Firm* — Scully, Scott, Murphy & Presser, P.C.

(57) ABSTRACT

A system includes an object in a space to generate an induced field; coils that generate a driving field; a detecting coil that detects a synthetic field of the driving field and the induced field; a unit that detects a driving current through the coil in synchronization with field detection by the detecting coil; a calculating unit that calculates a position and a direction of the object based on a detection value of the synthetic field and a detection value of the driving current; and a unit that calculates a phase of a driving field component which corresponds to the driving field at the detection value of the synthetic field, based on the detection value. The calculating unit obtains a component having a phase difference approximately orthogonal to the phase of the driving field component and calculates the position and direction of the object based on the obtained component.

15 Claims, 23 Drawing Sheets

FOREIGN PATENT DOCUMENTS

| | | |
|---|---|---|
| WO | WO 2007/043458 A1 | 4/2007 |
| WO | WO 2007/123217 A1 | 11/2007 |
| WO | WO 2009/041524 A1 | 4/2009 |

* cited by examiner

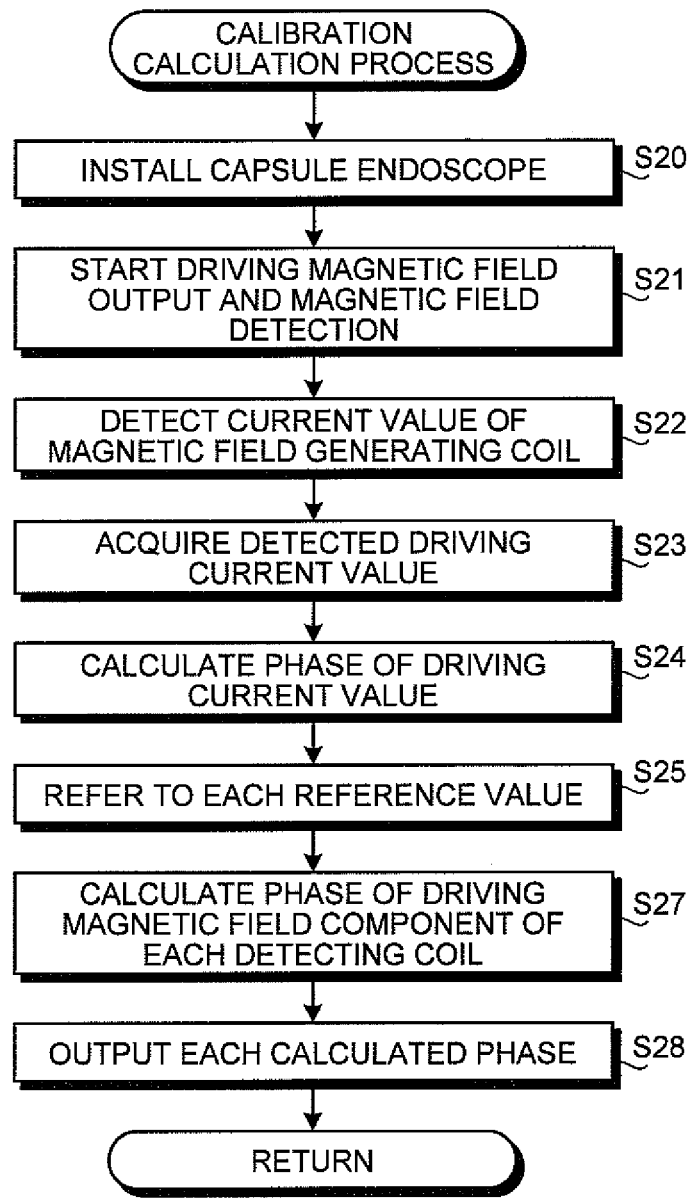

POSITION DETECTING SYSTEM AND POSITION DETECTING METHOD

CROSS-REFERENCE TO RELATED APPLICATIONS

This application is a continuation of PCT international application Ser. No. PCT/JP2011/050402 filed on Jan. 13, 2011 which designates the United States, incorporated herein by reference, and which claims the benefit of priority from Japanese Patent Application No. 2010-033664, filed on Feb. 18, 2010, incorporated herein by reference.

BACKGROUND OF THE INVENTION

1. Field of the Invention

The present invention relates to a position detecting system and a position detecting method, and particularly, to a position detecting system and a position detecting method, which detect the position of a capsule body-insertable apparatus to be introduced into a subject by using a magnetic field.

2. Description of the Related Art

In recent years, there has been developed a capsule detected object (hereinafter, referred to as a capsule endoscope) provided with an imaging element (for example, refer to Japanese Laid-open Patent Publication No. 2006-271520). The capsule endoscope, for example, is introduced into a subject via the oral route to capture an image of the interior of the subject, and transmits the acquired image (hereinafter, referred to as the in-vivo image) to an external device disposed out of the subject in a wireless manner. An operator visually recognizes the in-vivo image received in the external device, thereby diagnosing the condition and the like of the subject.

In a medical system using the capsule endoscope as described above, it is desired to accurately recognize the position, direction and the like of the capsule endoscope in order to specify a place to be imaged and guide the position of the capsule endoscope in the subject, for example. In this regards, Japanese Laid-open Patent Publication No. 2006-271520 has disclosed a position detecting system in which a resonant circuit (hereinafter, referred to as an LC resonant circuit) including a coil (L) and a capacitor (C) is provided in a capsule endoscope to detect a resonant magnetic field, which is generated by an alternating magnetic field (hereinafter, referred to as a driving magnetic field) applied from an exterior of the LC resonant circuit, using a detecting coil provided in the external device, thereby detecting the position and direction of the capsule endoscope.

SUMMARY OF THE INVENTION

A position detecting system according to an aspect of the present invention includes a detected object disposed in a detection space to generate an induced magnetic field in response to a driving magnetic field generated in the detection space; one or more magnetic field generating coils that generate the driving magnetic field in the detection space; a magnetic field detecting coil that detects a synthetic magnetic field of the driving magnetic field and the induced magnetic field generated by the detected object in response to the driving magnetic field; a current detecting unit that detects a driving current flowing through the magnetic field generating coil in synchronization with magnetic field detection by the magnetic field detecting coil; a position information calculating unit that calculates a position and a direction of the detected object based on a detection value of the synthetic magnetic field detected by the magnetic field detecting coil and a detection value of the driving current detected by the current detecting unit; and a calibration calculating unit that calculates a phase of a driving magnetic field component which corresponds to the driving magnetic field at the detection value of the synthetic magnetic field detected by the magnetic field detecting coil, based on the detection value of the driving current detected by the current detecting unit. The position information calculating unit obtains a component having a phase difference approximately orthogonal to the phase of the driving magnetic field component calculated by the calibration calculating unit, from the synthetic magnetic field detected by the magnetic field detecting coil, and calculates the position and direction of the detected object based on the obtained component.

A position detecting system according to another aspect of the present invention includes a detected object disposed in a detection space to generate an induced magnetic field in response to a driving magnetic field generated in the detection space; one or more magnetic field generating coils that generate the driving magnetic field in the detection space; a magnetic field detecting coil that detects a synthetic magnetic field of the driving magnetic field and the induced magnetic field generated by the detected object in response to the driving magnetic field; a current detecting unit that detects a driving current flowing through the magnetic field generating coil in synchronization with magnetic field detection by the magnetic field detecting coil; a position information calculating unit that calculates a position and a direction of the detected object based on a detection value of the synthetic magnetic field detected by the magnetic field detecting coil, and a detection value of the driving current detected by the current detecting unit; and a calibration calculating unit that calculates an amplitude and a phase of a driving magnetic field component, which corresponds to the driving magnetic field at the detection value of the synthetic magnetic field detected by the magnetic field detecting coil, based on the detection value of the driving current detected by the current detecting unit. The position information calculating unit obtains a difference between the synthetic magnetic field detected by the magnetic field detecting coil and the driving magnetic field based on the amplitude and the phase of the driving magnetic field component calculated by the calibration calculating unit, and calculates the position and direction of the detected object based on the obtained difference.

A position detecting method according to still another aspect of the present invention is for detecting a position of a detected object which is introduced into a detection space including at least one magnetic field generating coil for generating a driving magnetic field and generates an induced magnetic field in response to the driving magnetic field, and includes detecting a synthetic magnetic field of the driving magnetic field and the induced magnetic field generated by the detected object in response to the driving magnetic field; detecting a driving current flowing through the magnetic field generating coil in synchronization with detection of the synthetic magnetic field; calculating a phase of a driving magnetic field component corresponding to the driving magnetic field at a detection value of the synthetic magnetic field, based on a detection value of the driving current; and calculating a position and a direction of the detected object based on the detection value of the synthetic magnetic field and the phase of the driving magnetic field component. The calculating the position and the direction includes calculating the position and direction of the detected object based on a component obtained from the detected synthetic magnetic field, the component having a phase difference approximately orthogonal to the calculated phase of the driving magnetic field component.

A position detecting method according to still another aspect of the present invention is for detecting a position of a detected object which is introduced into a detection space including at least one magnetic field generating coil forming a driving magnetic field and generates an induced magnetic field in response to the driving magnetic field, and includes detecting a synthetic magnetic field of the driving magnetic field and the induced magnetic field, which is generated by the detected object in response to the driving magnetic field; detecting a driving current flowing through the magnetic field generating coil in synchronization with detection of the synthetic magnetic field; calculating an amplitude and a phase of a driving magnetic field component corresponding to the driving magnetic field at a detection value of the synthetic magnetic field, based on a detection value of the driving current; and calculating a position and a direction of the detected object based on the detection value of the synthetic magnetic field, and the amplitude and the phase of the driving magnetic field component. The calculating the position and the direction includes calculating the position and direction of the detected object based on a difference between the detected synthetic magnetic field and the driving magnetic field obtained based on the calculated amplitude and the phase of the driving magnetic field component.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a flowchart illustrating the procedure of a calibration calculation process illustrated in FIG. 4;

DETAILED DESCRIPTION OF THE PREFERRED EMBODIMENTS

Figure 1:
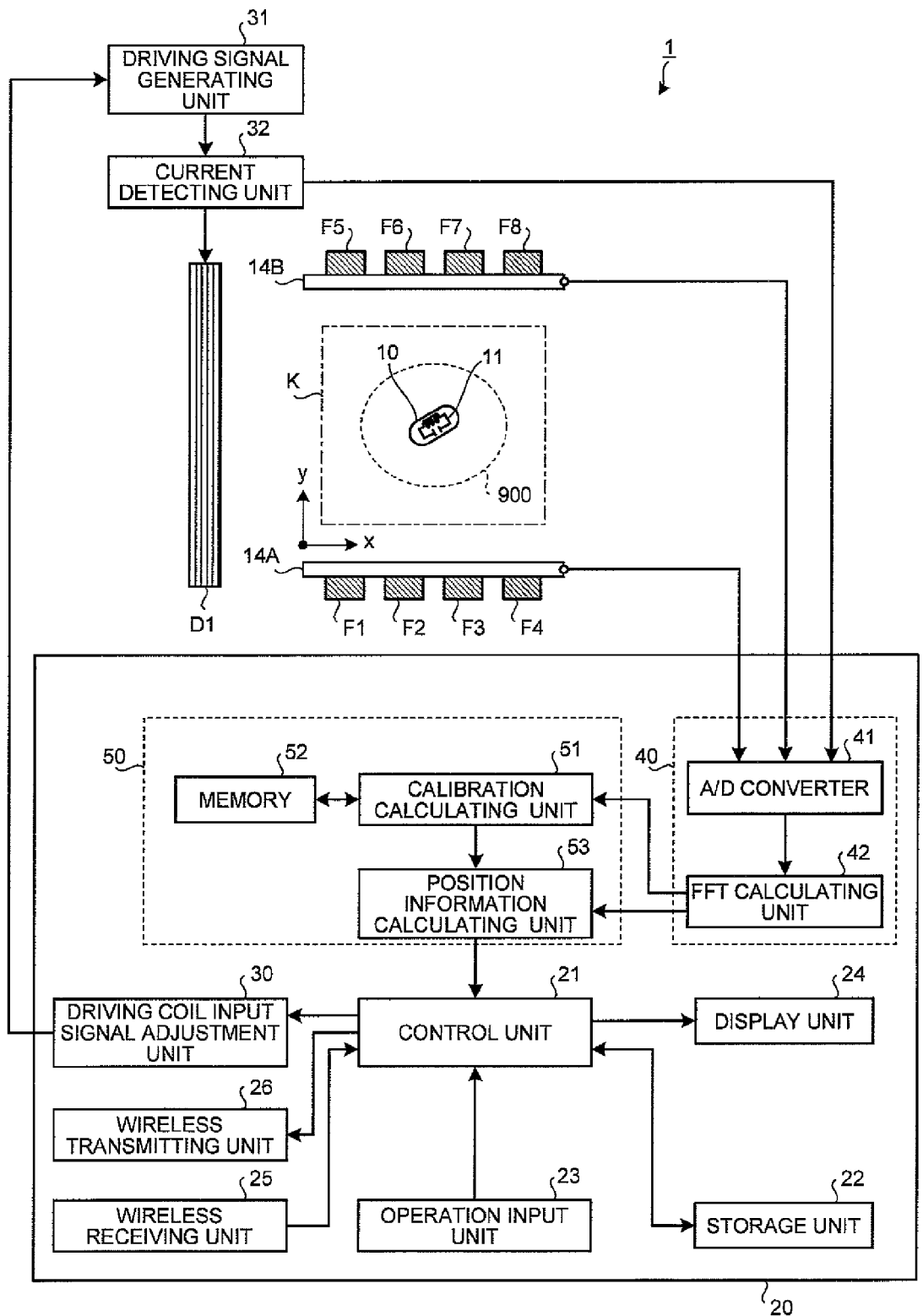
FIG. 1 is a schematic diagram illustrating the schematic configuration of a position detecting system according to a first embodiment.

Hereinafter, best embodiments of the present invention will be described in detail with reference to the accompanying drawings. In the following description, since each drawing schematically illustrates the shape, size, and position relation to a certain extent that the content of the present invention can be understood, the present invention is not limited only to the shape, size and, position relation illustrated in each drawing. Furthermore, in the drawings, the same reference numerals are used to designate the same elements.

First Embodiment

Hereinafter, the configuration and operation of a position detecting system 1 according to a first embodiment of the present invention will be described in detail with reference to the accompanying drawings. In addition, the present embodiment realizes a position detecting system and a position detecting method, which can obtain a driving magnetic field component actually generated and separate a resonant magnetic field component based on the driving magnetic field component, thereby accurately detecting the position of a detected object regardless of a time-dependent change of a driving magnetic field.

FIG. 1 is a schematic diagram illustrating the schematic configuration of the position detecting system 1 according to the first embodiment. As illustrated in FIG. 1, the position detecting system 1 according to the first embodiment includes a detection space K in which a subject 900 into which a capsule endoscope 10 serving as a detected object is introduced is located, and an external device 20 that detects the position and direction (posture) of the capsule endoscope 10 in the detection space K.

As illustrated in FIG. 1, the capsule endoscope 10 includes a resonant magnetic field generating unit 11 (refer to FIG. 1) that generates a resonant magnetic field for position detection. The resonant magnetic field generating unit 11 includes an LC resonant circuit including a capacitor (C) and an inductor (L), which are connected in parallel to each other as will be described later, is excited by a magnetic field (hereinafter, referred to as a driving magnetic field) for position detection, which has a frequency approximately the same as a resonant frequency input from an exterior, and generates a resonant magnetic field. In other words, the capsule endoscope 10 generates a resonant magnetic field which is an induced magnetic field in response to a driving magnetic field generated in the detection space K. In addition, the resonant frequency indicates a resonant frequency of the LC resonant circuit determined by the capacitor (C) and the inductor (L), which are connected in parallel to each other. Furthermore, the capsule endoscope 10, for example, may have a function as a capsule medical apparatus, receive a wireless signal indicating various operation instructions from the external device 20, and transmit in-vivo information, which is acquired by capturing the in-vivo image of a subject, to the external device 20 as a wireless signal.

Provided in the detection space K are a magnetic field generating coil D1 that generates a driving magnetic field in the detection space K with an approximately uniform distribution, a plurality of detecting coils F1 to F8 (hereinafter, a reference numeral of an arbitrary detecting coil will be referred to as S) for detecting a magnetic field generated in the detection space K, and wiring substrates 14A and 14B on which the plurality of detecting coils F1 to F4 and F5 to F8 are mounted, respectively. Furthermore, the wiring substrate 14A, for example, is installed below a mounting base (not illustrated) on which the subject 900 into which the capsule endoscope 10 is introduced is mounted, and the wiring substrate 14B, for example, disposed above the detection space K.

The magnetic field generating coil D1, for example, generates an approximately uniform driving magnetic field, which includes magnetic field lines extending in a predetermined axial direction in the detection space K, as a driving magnetic field generated in the detection space K. Each detecting coil F detects a magnetic field generated in the detection space K. When the capsule endoscope 10 is disposed in the detection space K, each detecting coil F detects a synthetic magnetic field of the resonant magnetic field, which is generated by the resonant magnetic field generating unit 11 of the capsule endoscope 10 in response to the driving magnetic field generated by the magnetic field generating coil D1, and the driving magnetic field generated by the magnetic field generating coil D1. A detection signal read from each detecting coil F indicates a signal which is obtained by representing magnetic field information, such as the strength and phase of a magnetic field at an installation position of each detecting coil F, by using a voltage. For example, each detecting coil F is a magnetic sensor including a coil capable of detecting magnetic field strength and direction in a predetermined axial direction. However, the present invention is not limited thereto. For example, each detecting coil F may be configured to include a magnetic sensor having a magnetoresistive element, a magnetoimpedance element (MI element), and the like. Furthermore, each detecting coil F may also be configured to include a 3-axis magnetic sensor including three coils for detecting an x axis, a y axis, and a z axis, respectively, and the like. The plurality of detecting coils F are installed at positions where they are less affected by the influence of the driving magnetic field and can easily detect the resonant magnetic field generated by the resonant magnetic field generating unit 11 of the capsule endoscope 10. The first embodiment illustrates an example in which the plurality of detecting coils F1 to F4 are two-dimensionally disposed on the bottom surface (an x-y plane below the detection space K) of the wiring substrate 14A disposed below the detection space K, and the plurality of detecting coils F5 to F8 are two-dimensionally disposed on the upper surface (an x-y plane above the detection space K) of the wiring substrate 14B disposed above the detection space K.

Furthermore, the external device 20 include a control unit 21, a storage unit 22, an operation input unit 23, a display unit 24, a wireless receiving unit 25, and a wireless transmitting unit 26. The control unit 21 controls each element of the external device 20. The storage unit 22 stores various programs, parameters and the like executed when the control unit 21 controls each element. The operation input unit 23 allows an operator to input various operation instructions for the capsule endoscope 10. The display unit 24 displays the position or direction of the capsule endoscope 10 and in-vivo information, which is acquired from the capsule endoscope 10, using an image (includes a moving image) or sound. The wireless receiving unit 25 receives the in-vivo information and the like, which are transmitted from the capsule endoscope 10 as a wireless signal. The wireless transmitting unit 26 transmits various operation instructions, such as a image capturing instruction to the capsule endoscope 10, as a wireless signal.

In addition, the external device 20 includes a driving coil input signal adjustment unit 30, a driving signal generating unit 31, a current detecting unit 32, a converter 40, and a position detecting unit 50. The driving coil input signal adjustment unit 30 adjusts the amplitude or phase of a signal used for driving the magnetic field generating coil D1. The driving signal generating unit 31 produces a driving signal, which is input to the magnetic field generating coil D1, under the control of the driving coil input signal adjustment unit 30. The current detecting unit 32 detects a driving current, which flows through the magnetic field generating coil D1, in synchronization with magnetic field detection by the detecting coils F. The converter 40 performs A/D conversion and Fourier transform with respect to a voltage variation read by the detecting coils F, separates a predetermined frequency component, and outputs a synthetic magnetic field component. Furthermore, the converter 40 performs A/D conversion and Fourier transform with respect to a current variation read by the current detecting unit 32, separates a predetermined frequency component, and outputs a driving current component. Based on synthetic magnetic field components detected by the detecting coils F and the driving current component detected by the current detecting unit 32, the position detecting unit 50 acquires resonant magnetic field components of the capsule endoscope 10, which are included in the synthetic magnetic field components, and calculates the position and direction of the capsule endoscope 10. In addition, FIG. 1 illustrates a configuration, in which the driving signal generating unit 31 is provided separately from the external device 20, as an example. However, the present invention is not limited thereto. The driving signal generating unit 31 may be provided in the external device 20.

The control unit 21, for example, includes a CPU, an MPU and the like, and controls each element of the external device 20 according to a program and a parameter which are read from the storage unit 22. Furthermore, the storage unit 22, for example, includes a RAM, a ROM and the like, and holds a program and a parameter executed when the control unit 21 controls each element. The storage unit 22 appropriately stores the in-vivo image, which is received from the capsule endoscope 10, information on the position or direction of the capsule endoscope 10, which is derived by the position detecting unit 50, and the like.

The operation input unit 23, for example, includes a keyboard, a mouse, a numeral keypad, joystick and the like, and allows an operator to input various operation instructions, such as an image capturing instruction (includes other in-vivo information acquisition instructions) for the capsule endoscope 10, various operation instructions, such as a screen switching instruction for switching a screen displayed on the display unit 24 for the external device 20, and the like. In addition, when the capsule endoscope 10 includes various imaging units and an image acquired by the capsule endoscope 10 is displayed on the display unit 24 in approximately real time, the operation input unit 23 may further has a function of switching the screen displayed on the display unit 24.

The display unit 24, for example, includes a display device such as a liquid crystal display, a plasma display, or an LED array, and displays information on the position, direction and the like of the capsule endoscope 10, and in-vivo information such as the in-vivo image transmitted from the capsule endoscope 10. Furthermore, the display unit 24 may also have a sound playback function using a speaker and the like. The display unit 24 informs an operator of various types of operation guidance and information (includes an alarm and the like) on a battery level and the like of the capsule endoscope 10 with the sound by using the sound playback function.

The wireless receiving unit 25 is connected to a receiving antenna (not illustrated) including a dipole antenna and the like disposed adjacent to the detection space K. The receiving antenna, for example, is disposed adjacent to the detection space K. The wireless receiving unit 25 receives the in-vivo image and the like transmitted from the capsule endoscope 10 as a wireless signal via the receiving antenna, performs various processes, such as filtering, down-conversion, demodulation, and decoding, with respect to the received signal, and outputs a resultant signal to the control unit 21.

The wireless transmitting unit 26 is connected to a transmitting antenna (not illustrated) including a dipole antenna and the like disposed adjacent to the detection space K. The transmitting antenna, for example, is disposed adjacent to the detection space K. The wireless transmitting unit 26 performs various processes, such as superposition, modulation, or up-conversion to a reference frequency signal for transmission, with respect to various operation instruction signals for the capsule endoscope 10, which are input from the control unit 21, and transmits a resultant signal to the capsule endoscope 10 as an electric wave signal from the transmitting antenna.

The driving coil input signal adjustment unit 30 calculates a signal waveform with a frequency, which is approximately the same as the resonant frequency of the LC resonant circuit of the capsule endoscope 10, according to a control signal input from the control unit 21, and outputs the signal waveform to the driving signal generating unit 31.

The driving signal generating unit 31 produces a driving signal according to the signal waveform input from the driving coil input signal adjustment unit 30, current-amplifies the driving signal, and inputs an amplified driving signal to the magnetic field generating coil D1. The magnetic field generating coil D1 having received the amplified driving signal generates a magnetic field, which has a frequency approximately the same as the resonant frequency of the LC resonant circuit of the capsule endoscope 10, thereby generating a driving magnetic field which excites the LC resonant circuit in the detection space K.

The current detecting unit 32 detects the driving current, which flows through the magnetic field generating coil D1, in synchronization with the magnetic field detection by the detecting coils F, and outputs the driving current to the converter 40. Furthermore, a detection signal output from the current detecting unit 32 indicates a signal which is obtained by representing information on the strength, phase and the like of the driving current, which flows through the magnetic field generating coil D1, by a current. In addition, the detection signal output from the current detecting unit 32 may indicate a signal which is obtained by representing the information on the strength, phase and the like of the driving current, which flows through the magnetic field generating coil D1, by a voltage.

The converter 40 performs a predetermined process with respect to the detection signal which indicates the voltage variation read by the detecting coils F, thereby deriving a predetermined frequency component corresponding to the synthetic magnetic field component included in the detection signal in approximately real time. Furthermore, the converter 40 performs a predetermined process with respect to the detection signal which indicates the current variation read by the current detecting unit 32, thereby deriving a predetermined frequency component corresponding to the driving current in approximately real time.

The converter 40, for example, includes an A/D converter 41 and an FFT calculating unit 42. The A/D converter 41 reads each detection signal from the plurality of detecting coils F and the current detecting unit 32, and appropriately performs amplification, band limitation, and A/D conversion with respect to the read analog detection signals. Furthermore, the FFT calculating unit 42 performs fast Fourier transform with respect to digital detection signals output from the A/D converter 41, thereby generating data (hereinafter, referred to as FFT data) indicating each synthetic magnetic field component detected by each detecting coil F, and the driving current detected by the current detecting unit 32. The FFT calculating unit 42 inputs the FFT data, which indicates each synthetic magnetic field component detected by each detecting coil F, to a calibration calculating unit 51 and a position information calculating unit 53 of the position detecting unit 50. Furthermore, the FFT calculating unit 42 inputs FFT data indicating the driving current detected by the current detecting unit 32 to the calibration calculating unit 51 of the position detecting unit 50. Furthermore, the FFT data is obtained by converting magnetic field information, which is included in the detection signals read from the detecting coils F, or driving current information, which is included in the detection signal read from the current detecting unit 32, into information including strength and phase components.

The position detecting unit 50 performs a predetermined calculation process with respect to the FFT data input from the converter 40, thereby deriving the current position or direction of the capsule endoscope 10 from the magnetic field information included in the detection signals.

Here, the detection signal read from each detecting coil F at the time of position detection of the capsule endoscope 10 includes a driving magnetic field component, which is a driving magnetic field component generated by the magnetic field generating coil D1 and has a frequency approximately the same as the resonant frequency, in addition to the resonant magnetic field component generated by the LC resonant circuit. Therefore, it is not possible to derive the accurate position or direction of the capsule endoscope 10 (particularly, the LC resonant circuit) from the FFT data corresponding to each detecting coil F. In this regards, it is necessary for the position detecting unit 50 to separate a driving magnetic field component from a detection value of the synthetic magnetic field by each detecting coil F, and obtain a resonant magnetic field component corresponding to the resonant magnetic field generated by the LC resonant circuit.

In the present first embodiment, the position detecting unit 50 obtains a driving magnetic field component corresponding to the resonant magnetic field actually generated by the magnetic field generating coil D1, other than a driving magnetic field in the state in which no LC resonant circuit detected in advance exists, separates the obtained driving magnetic field component from a synthetic magnetic field, and acquires a resonant magnetic field component actually generated by the LC resonant circuit of the capsule endoscope 10.

The position detecting unit 50 includes the calibration calculating unit 51, a memory 52 for storing a predetermined reference value, and the position information calculating unit 53. The calibration calculating unit 51 calculates the phase of the driving magnetic field component at the detection value of the synthetic magnetic field component detected by the detecting coil F based on the detection value of the driving current detected by the current detecting unit 32. The position information calculating unit 53 obtains a component, which has a phase difference approximately orthogonal to the phase of the driving magnetic field component calculated by the calibration calculating unit 51, from the synthetic magnetic field detected by the detecting coil F, and calculates the position and direction of the capsule endoscope 10 based on the obtained component.

With reference to FIG. 2, the process content of each element of the position detecting unit 50 will be described. First, the synthetic magnetic field detected by the detecting coil F includes both the resonant magnetic field generated by the resonant magnetic field generating unit 11 of the capsule endoscope 10 in response to the driving magnetic field generated by the magnetic field generating coil D1, and the driving magnetic field generated by the magnetic field generating coil D1 itself. That is, the detecting coil F detects the driving magnetic field generated by the magnetic field generating coil D1 regardless of whether the capsule endoscope 10 is in the detection range K. The driving magnetic field component detected by the detecting coil F has a relation to be a pair with respect to the driving magnetic field, which is generated by the magnetic field generating coil D1, based on the relative position relation between the magnetic field generating coil D1 and the detecting coil F.

Figure 2A:
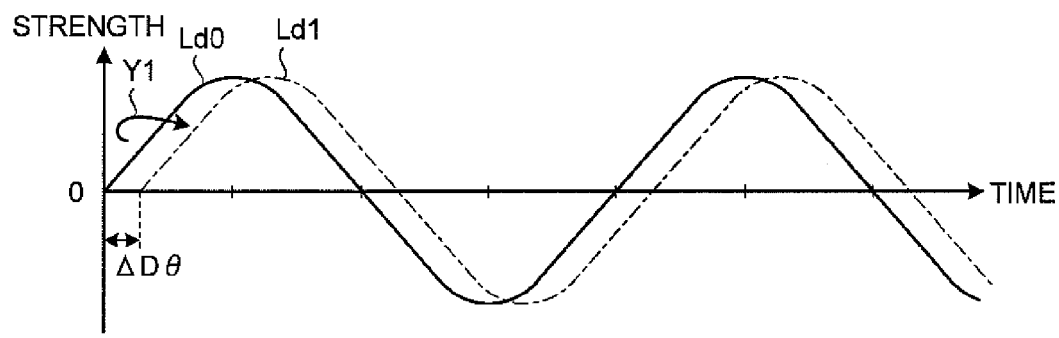
FIG. 2A is a diagram illustrating time dependence with respect to the strength of a driving magnetic field generated by a magnetic field generating coil.
Figure 2B:
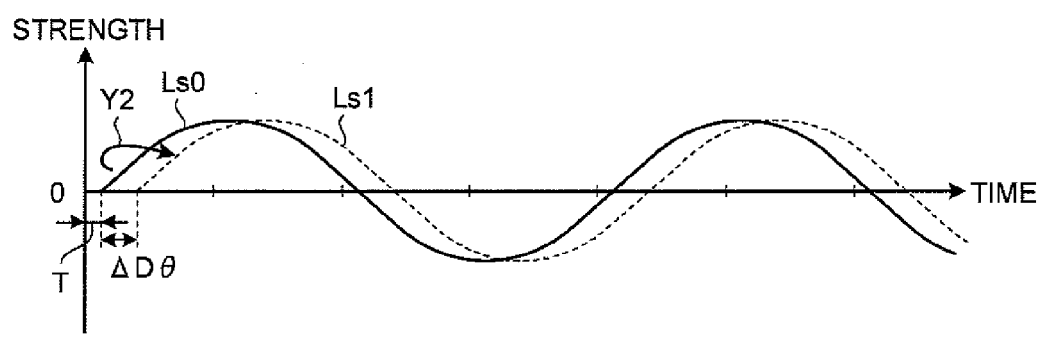
FIG. 2B is a diagram illustrating time dependence with respect to the strength of a driving magnetic field detected by a detecting coil.
Figure 2C:
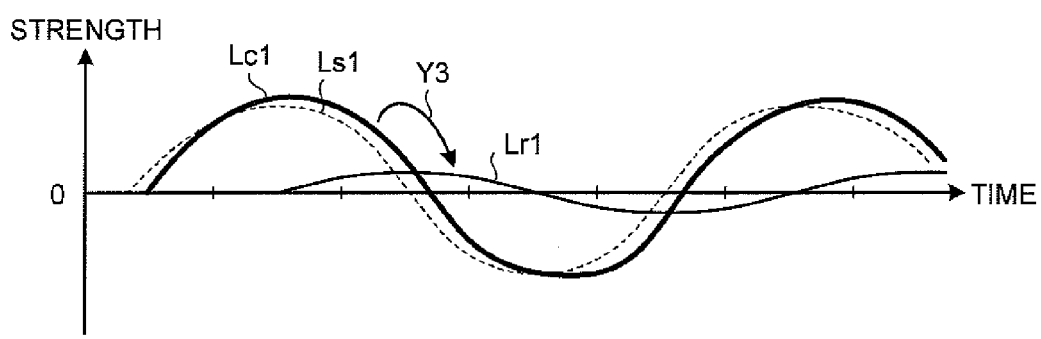
FIG. 2C is a diagram illustrating time dependence with respect to the strength of a synthetic magnetic field detected by a detecting coil.

FIG. 2A is a diagram illustrating time dependence with respect to the strength of the driving magnetic field generated by the magnetic field generating coil D1, FIG. 2B is a diagram illustrating time dependence with respect to the strength of the driving magnetic field detected by the detecting coil F, and FIG. 2C is a diagram illustrating time dependence with respect to the strength of the synthetic magnetic field detected by the detecting coil. FIG. 2B illustrates the detection result of the detecting coil F when the capsule endoscope 10 is not positioned in the detection range K.

For example, when the magnetic field generating coil D1 has generated a driving magnetic field at a predetermined frequency as indicated by a curved line Ld0 of FIG. 2A, the detecting coil F detects a driving magnetic field at the same frequency in the state in which the driving magnetic field is shifted by time T as indicated by a curved line Ls0 of FIG. 2B. The correspondence relation is determined by the characteristics of the magnetic field generating coil D1, the characteristics of the detecting coil F, and relative position relation between the magnetic field generating coil D1 and the detecting coil F. Thus, when the driving magnetic field generated by the magnetic field generating coil D1 is generated with a phase, which is shifted by $\Delta D\theta$ as indicated by an arrow Y1 as compared with the curved line Ld0, due to a time-dependent change as indicated by a curved line Ld1 of FIG. 2A, the detecting coil F detects a driving magnetic field with a phase, which is shifted by $\Delta D\theta$ as indicated by an arrow Y2 as compared with the curved line Ls0, as indicated by a curved line Ls1 of FIG. 2B.

Consequently, after the driving magnetic field generated by the magnetic field generating coil D1, and the detection result of the driving magnetic field detected by the detecting coil F in such a case are obtained in advance as a reference, if a variation of the phase of the driving magnetic field actually generated by the magnetic field generating coil D1 from the phase of the driving magnetic field serving as the reference is obtained in order to detect the position of the capsule endoscope 10, it is possible to obtain the phase of a component corresponding to the driving magnetic field of the synthetic magnetic field detected by the detecting coil F. The phase of the component corresponding to the driving magnetic field of the synthetic magnetic field detected by the detecting coil F is also shifted from the reference by the same degree as the driving magnetic field actually generated by the magnetic field generating coil D1. The synthetic magnetic field includes the driving magnetic field component corresponding to the driving magnetic field, and the resonant magnetic field component from the capsule endoscope 10. Consequently, the phase of one driving magnetic field component of the synthetic magnetic field detected by the detecting coil F is obtained, so that the driving magnetic field component indicated by the curved line Ls1 is separated from the synthetic magnetic field as indicated by a curved line Lc1 of FIG. 2C, thereby acquiring the resonant magnetic field component, which is generated by the capsule endoscope 10 as indicated by a curved line Lr1, as indicated by an arrow Y3.

Meanwhile, the phase of the driving magnetic field in the magnetic field generating coil D1 is the same as the phase of the current flowing through the magnetic field generating coil D1. Thus, in the present first embodiment, the current detecting unit 32 is provided to detect the driving current, which flows through the magnetic field generating coil D1, as a value representing the driving magnetic field generated by the magnetic field generating coil D1. That is, in the present first embodiment, the phase of the driving current, which flows through the magnetic field generating coil D1 and is detected by the current detecting unit 32, is obtained, thereby obtaining the phase of the driving magnetic field actually generated by the magnetic field generating coil D1.

Specifically, first, in the state in which the capsule endoscope 10 is not positioned in the detection space K, the driving magnetic field is generated from the magnetic field generating coil D1, and is actually detected by each detecting coil F in such a state. In such a case, the current detecting unit 32 detects the driving current, which flows through the magnetic field generating coil D1, in synchronization with the magnetic field detection of each detecting coil F. In the present first embodiment, a detection value of the magnetic field detected by the detecting coil F and a detection value of the driving current detected by the current detecting unit 32 in the state, in which the capsule endoscope 10 is not positioned in the detection space K, are used as reference values. In addition, the memory 52 stores, as the reference values, the detection value of the magnetic field detected by the detecting coil F and the detection value of the driving current detected by the current detecting unit 32 in the state in which the capsule endoscope 10 is not positioned in the detection space K.

Then, the calibration calculating unit 51 calculates the phase of the driving magnetic field component based on the detection value of the driving current, which is detected by the current detecting unit 32, during the position detection of the capsule endoscope 10, and the reference values stored in the memory 52. Specifically, the calibration calculating unit 51 calculates a phase difference between the detection value of the driving current, which is stored in the memory 52 as the reference value, and the detection value of the driving current, which actually flows through the magnetic field generating coil D1 and is detected by the current detecting unit 32. Then, the calibration calculating unit 51 calculates the phase of the driving magnetic field component using the obtained phase difference. In other words, the calibration calculating unit 51 calculates a value obtained by adding the calculated phase difference to the phase of the driving magnetic field component stored as the reference value, and outputs the value to the position information calculating unit 53 as the phase of the driving magnetic field component of the driving magnetic field actually generated by the magnetic field generating coil D1.

Figure 3:
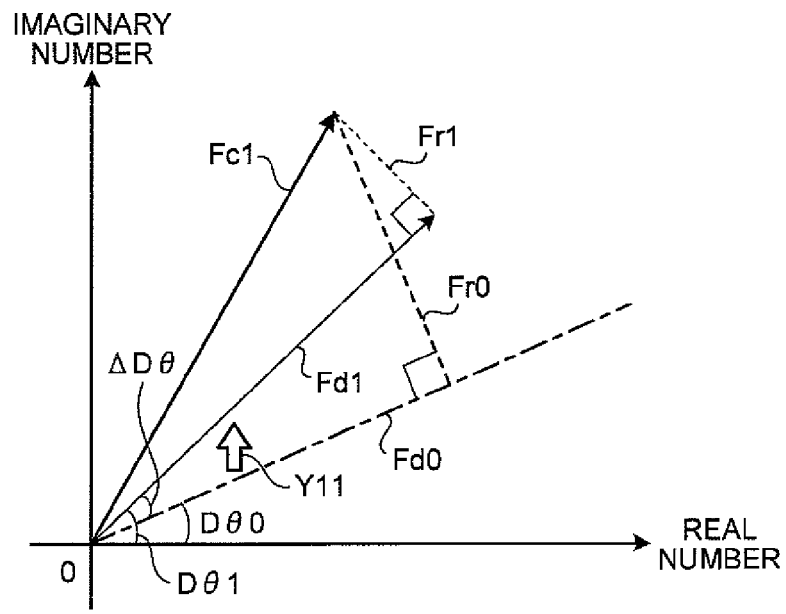
FIG. 3 is a diagram illustrating the relation among a driving magnetic field by the magnetic field generating coil illustrated in FIG. 1, a synthetic magnetic field which is a magnetic field detected by a detecting coil, and a resonant magnetic field of a capsule endoscope.

Next, with reference to FIG. 3, a process will be described, in which the position information calculating unit 53 derives the current position or direction of the capsule endoscope 10. FIG. 3 is a diagram illustrating the relation among a driving magnetic field by the magnetic field generating coil D1, the synthetic magnetic field which is a magnetic field detected by the detecting coil F, and the resonant magnetic field of the capsule endoscope 10.

As illustrated in FIG. 3, a resonant magnetic field (hereinafter, a vector of a resonant magnetic field developed on a planar space indicating a strength and a phase will be referred to as Fr) generated by the capsule endoscope 10 has a phase difference of 90 degrees relative to a driving magnetic field (hereinafter, a vector of a driving magnetic field developed on the planar space indicating the strength and the phase will be referred to as Fd). Therefore, in order to take the resonant magnetic field Fr by removing the driving magnetic field Fd from a full magnetic field (hereinafter, referred to as a detected synthetic magnetic field, and a vector of the synthetic magnetic field developed on a planar space indicating a strength and a phase will be referred to as Fc1) included in the FFT data, it is necessary to extract a vector component having a phase difference of 90 degrees relative to the driving magnetic field Fd from the synthetic magnetic field Fc1.

The position information calculating unit 53 separates the resonant magnetic field Fr1, which has a phase difference of 90 degrees relative to the driving magnetic field Fd1 corresponding to the phase of the driving magnetic field component output from the calibration calculating unit 51, from the synthetic magnetic field Fc1, and performs a predetermined calculation process with respect to the resonant magnetic field Fr1, thereby deriving the current position or direction of the capsule endoscope 10.

Conventionally, in the state in which a capsule endoscope is not introduced into the detection space K, a magnetic field generating coil is driven to form a driving magnetic field in the detection space, a driving magnetic field Fd0 detected by a detecting coil is obtained in advance in such a state, and a phase component of the driving magnetic field Fd0 is used as a driving magnetic field removed from the synthetic magnetic field Fc1.

However, in the conventional method, even when the driving magnetic field actually generated by the magnetic field generating coil is changed into a driving magnetic field Fd1 with a phase D$\theta$1, which is shifted from the driving magnetic field Fd0 by $\Delta$D$\theta$ as indicated by an arrow Y11 due to a time-dependent change of the magnetic field generating coil, a temperature change, and interference with an LC resonant circuit, the driving magnetic field Fd0 is used as a driving magnetic field removed from the synthetic magnetic field Fc. Therefore, in the conventional method, the phase of the driving magnetic field actually generated by the magnetic field generating coil may be different from the phase of a driving magnetic field component to be removed, and accurate separation is not possible, resulting in the deterioration of position detection accuracy. That is, in the conventional method, a vector component, which has a phase difference of 90degrees relative to the driving magnetic field Fd0 obtained in advance other than the driving magnetic field Fd1 actually generated by the magnetic field generating coil D1, is extracted from the synthetic magnetic field Fc1, and taken as a resonant magnetic field Fr0. Thus, in the conventional method, even when the driving magnetic field Fd0 is changed into the driving magnetic field Fd1 due to a time-dependent change of the driving magnetic field generating unit, a temperature change, and interference with an LC resonant circuit, since a change in the driving magnetic field is not reflected in the separation process of a resonant magnetic field and position detection is performed using the magnetic field Fr0 different from the actual resonant magnetic field Fr1, position detection accuracy may deteriorate.

On the other hand, in the present first embodiment, other than the driving magnetic field Fd0 before being changed, the phase of the driving magnetic field Fd1 actually generated by the magnetic field generating coil D1 is obtained based on the driving current, which flows through the magnetic field generating coil D1 and is detected by the current detecting unit 32, and a resonant magnetic field is separated using the phase of the obtained driving magnetic field Fd1. Consequently, in the present first embodiment, the phase of the driving magnetic field actually generated by the magnetic field generating coil D1 is not different from the phase of the driving magnetic field component to be removed, and the resonant magnetic field Fr1 can be correctly separated from the synthetic magnetic field Fc1. Thus, in the present first embodiment, even when a change occurs in the driving magnetic field, which is generated by the magnetic field generating coil D1, due to a time-dependent change of the magnetic field generating coil D1, a temperature change, and interference with an LC resonant circuit, it is possible to accurately separate the resonant magnetic field Fr1 from the driving magnetic field Fd1, resulting in the accurate detection of the position of a detected object.

Furthermore, in the present first embodiment, a detection value of a driving magnetic field and a detection value of a driving current are obtained as reference values in the state in which the capsule endoscope 10 is not actually positioned in the detection space K in the position detecting system 1, a detection value of the current detecting unit 32 is added during the position detection, and a driving magnetic field component is obtained using the reference values. In other words, the reference values include an individual difference of the position detecting system 1 and the influence of a peripheral environment of the position detecting system 1, and are set for each position detecting system 1. In the first embodiment, position detection is performed using the reference value obtained for each position detecting system 1, so that it is possible to achieve an accurate position detection result excluding the individual difference of the position detecting system 1 and the influence of the peripheral environment of the position detecting system 1.

Figure 4:
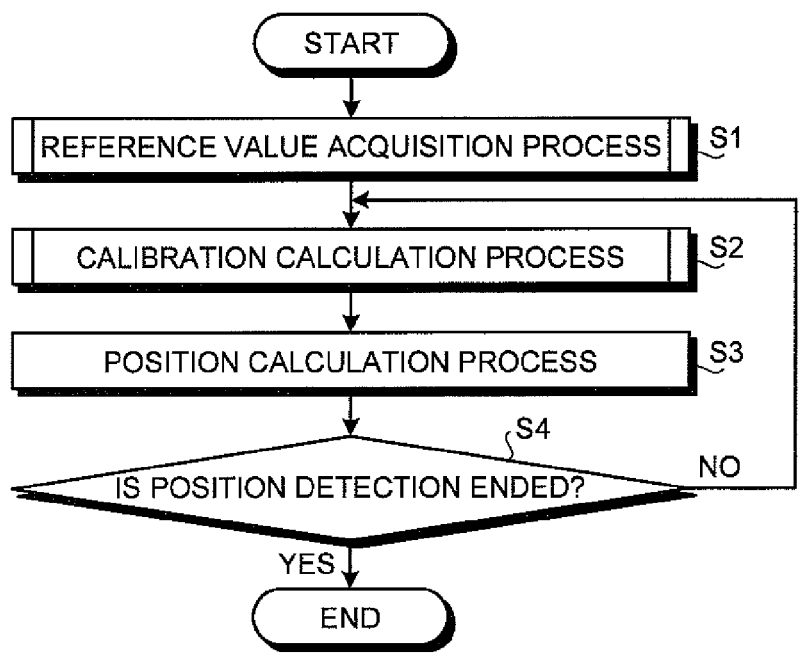
FIG. 4 is a flowchart illustrating the procedure of a position detection process in the position detecting system illustrated in FIG. 1.

Next, with referenced to FIG. 4, a position detection process of the position detecting system 1 illustrated in FIG. 1 will be described. FIG. 4 is a flowchart illustrating the procedure of the position detection process in the position detecting system 1 illustrated in FIG. 1.

As illustrated in FIG. 4, the position detecting system 1 performs a reference value acquisition process of acquiring a detection value of a driving magnetic field detected by each detecting coil F and a detection value of a driving current detected by the current detecting unit 32 as reference values in the case in which the capsule endoscope 10 is not positioned in the detection space K (step S1). The reference value acquisition process is not necessary to be performed for each position detection, and is only necessary to be performed when the position detecting system 1 is installed, and parts of the magnetic field generating coil D1 and the detecting coil F are exchanged. Furthermore, the reference value acquisition process may be periodically performed in order to hold constant accuracy.

The position detecting system 1 performs a position detection process of detecting the position of the capsule endoscope 10 in the state in which the capsule endoscope 10 is actually disposed in the detection space K. In such a case, in the position detecting system 1, the calibration calculating unit 51 performs a calibration calculation process of calculating the phase of a driving magnetic field component of a synthetic magnetic field detected by each detecting coil F (step S2). Then, the position information calculating unit 53 performs a position calculation process of obtaining a component, which has a phase difference approximately orthogonal to the phase of the driving magnetic field component calculated by the calibration calculating unit 51, from the synthetic magnetic field detected by the detecting coil F, and calculating the position and direction of a detected object based on the obtained component (step S3). The calculating result of the position and direction by the position information calculating unit 53 is output to the control unit 21, and then is output to the display unit 24 under the control of the control unit 21.

Then, the control unit 21 determines whether the position detection process has been completed based on an instruction input from the operation input unit 23 (step S4). When it is determined that the position detection process has not been completed (step S4: No), the control unit 21 returns to step S2 in order to continue the position detection process, and performs the calibration calculation process. Meanwhile, when it is determined that the position detection process has been completed (step S4: Yes), the control unit 21 also completes a control process for the magnetic field generating coil D1, the detecting coil F, the converter 40, and the position detecting unit 50, together with the completion of the position detection.

Figure 5:
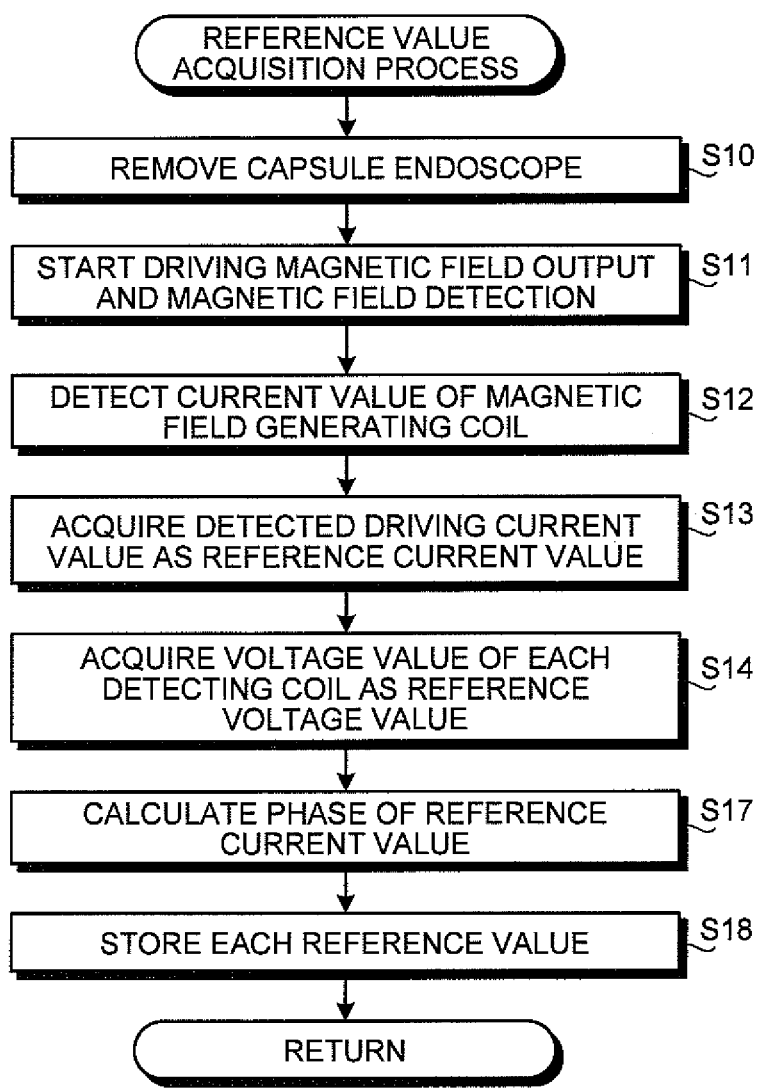
FIG. 5 is a flowchart illustrating the procedure of a reference value acquisition process illustrated in FIG. 4.

Next, the reference value acquisition process illustrated in FIG. 4 will be described. FIG. 5 is a flowchart illustrating the procedure of the reference value acquisition process illustrated in FIG. 4. As illustrated in FIG. 5, in the reference value acquisition process, the capsule endoscope 10 is taken out of the detection space K in order to prevent the capsule endoscope 10 from being positioned in the detection space K (step S10). Next, the magnetic field generating coil D1 performs a driving magnetic field output process of generating a driving magnetic field in the detection space K under predetermined conditions under the control of the control unit 21, and the detecting coil F also starts magnetic field detection together with the execution of the driving magnetic field output process (step S11).

Then, the current detecting unit 32 detects a current value of a driving current flowing through the magnetic field generating coil D1 (step S12). In addition, the current detecting unit 32 detects the current value in synchronization with the magnetic field detection of each detecting coil F. The driving current value detected by the current detecting unit 32 is subject to A/D conversion by the A/D converter 41 and is further subject to Fourier transform by the FFT calculating unit 42. As a result, a predetermined frequency component used in position detection is separated, and in this state, a real number value and an imaginary number value are output to the calibration calculating unit 51. The calibration calculating unit 51 acquires the driving current value detected by the current detecting unit 32 and after the conversion by the converter 40 as a reference current value (step S13). Meanwhile, in the same manner, each voltage value corresponding to the magnetic field detected by each detecting coil F is subject to the A/D conversion by the A/D converter 41 and is further subject to the Fourier transform by the FFT calculating unit 42. As a result, a predetermined frequency component used in the position detection is separated, and in this state, a real number value and an imaginary number value are output to the calibration calculating unit 51. The calibration calculating unit 51 acquires each voltage value, which corresponds to the magnetic field detected by each detecting coil F and after the conversion by the converter 40, as a reference voltage value corresponding to each detecting coil F (step S14).

Then, the calibration calculating unit 51 calculates the phase of the acquired reference current value (step S17). The calibration calculating unit 51 stores the reference current value, each reference voltage value, and the phase of the reference current value in the memory 52 as reference values (step S18), and completes the reference value acquisition process.

Next, the calibration calculation process illustrated in FIG. 4 will be described. FIG. 6 is a flowchart illustrating the procedure of the calibration calculation process illustrated in FIG. 4. As illustrated in FIG. 6, in the calibration calculation process, in order to start a position detection process, the subject 900 having the capsule endoscope 10 therein is moved to the detection space K and installed in the detection space K such that the capsule endoscope 10 is positioned in the detection space K (step S20). Then, the magnetic field generating coil D1 starts the driving magnetic field output process of generating the driving magnetic field in the detection space K under predetermined conditions under the control of the control unit 21, and each detecting coil F starts the magnetic field detection process together with the start of the driving magnetic field output process (step S21). In addition, the voltage value corresponding to the magnetic field detected by each detecting coil F is subject to the A/D conversion by the A/D converter 41 and is further subject to the Fourier transform by the FFT calculating unit 42, so that a predetermined frequency component used in the position detection is separated, and is output to the position information calculating unit 53 as the synthetic magnetic field detected by each detecting coil F.

Then, the current detecting unit 32 detects the current value of the driving current flowing through the magnetic field generating coil D1 (step S22). In addition, the current detecting unit 32 performs the current detection in synchronization with the magnetic field detection of each detecting coil F. The driving current value detected by the current detecting unit 32 is subject to A/D conversion by the A/D converter 41 and is further subject to Fourier transform by the FFT calculating unit 42, so that a predetermined frequency component is separated, and is output to the calibration calculating unit 51. The calibration calculating unit 51 acquires the driving current value detected by the current detecting unit 32 and after the conversion by the converter 40 (step S23), and calculates the phase of the driving current value (step S24). Then, the calibration calculating unit 51 refers to each reference value in the memory 52 (step S25).

The calibration calculating unit 51 calculates the phases of the driving magnetic field components of the synthetic magnetic field, which is detected by each detecting coil F, based on the phase of the calculated driving current value and the referred reference values (step S27). Then, the calibration calculating unit 51 outputs the calculated phases, that is, the phases of the driving magnetic field components of the synthetic magnetic field detected by each detecting coil F to the position information calculating unit 53 (step S28). The position information calculating unit 53 performs a separation process, which separates a resonant magnetic field with a phase difference of 90 degrees relative to the driving magnetic field corresponding to the phase of the driving magnetic field component output from the calibration calculating unit 51, from the synthetic magnetic field, for each detection result by each detecting coil F, and performs a predetermined calculation process with respect to the separated resonant magnetic field, thereby deriving the current position or direction of the capsule endoscope 10.

Next, the calculation processes of step S27 and step S28 will be described using the detecting coil F1 of the detecting coils F as an example. In addition, the phase of the reference current value stored in the memory 52 is set as D$\theta$, a real number value of the reference voltage value in the detecting coil F1 is set as DR1, an imaginary number value of the reference voltage value in the detecting coil F1 is set as DI1, and the phase of the driving current value detected by the current detecting unit 32 is set as D$\theta$'.

First, the calibration calculating unit 51 calculates the phase difference $\Delta D\theta$ between the reference current value and the driving current value by using Equation (1) below.

$$D\theta' - D\theta = \Delta D\theta \tag{1}$$

Next, the calibration calculating unit 51 calculates a real number value SR1' and an imaginary number value SI1' of a driving voltage value, which corresponds to the phase of the driving magnetic field component of the synthetic magnetic field detected by the detecting coil F1, by using the phase difference $\Delta D\theta$ obtained by Equation (1) and the reference voltage value. Specifically, by means of Equation (2) and Equation (3) below, the phase of each reference voltage value is added to each value of the reference voltage value by $\Delta D\theta$, thereby calculating the real number value SR1' and the imaginary number value SI1' of the driving voltage value.

$$SR1' = (SR1 \times \cos \Delta\theta - SI1 \times \sin \Delta\theta) \tag{2}$$

$$SI1' = (SR1 \times \sin \Delta\theta + SI1 \times \cos \Delta\theta) \tag{3}$$

Then, the calibration calculating unit 51 calculates the phase of the driving voltage value in the detecting coil F1 based on the real number value SR1' and the imaginary number value SI1' of the driving voltage value, which are calculated using Equation (2) and Equation (3). In the same manner, for the detecting coils F2 to F8, the calibration calculating unit 51 calculates the phase of each driving voltage value in the detecting coils F2 to F8.

The position detecting system 1 performs the procedures illustrated in FIGS. 4 to 6, obtains the phase of a driving magnetic field component for the driving magnetic field, which is actually generated by the magnetic field generating coil D1, as a driving magnetic field component constituting the synthetic magnetic field detected by each detecting coil F, and accurately separates the resonant magnetic field generated by the capsule endoscope 10 from the synthetic magnetic field based on the obtained phase of the driving magnetic field component, thereby accurately detecting the position of the capsule endoscope 10.

First Modification According to First Embodiment

Next, a first modification of the first embodiment will be described. In the first modification of the first embodiment, the case will be described in which a resonant magnetic field is separated by subtracting a driving magnetic field component from a synthetic magnetic field. In the first modification according to the first embodiment, the calibration calculating unit 51 also obtains the amplitude of a driving voltage value, in addition to the phase of the driving voltage value, which corresponds to a driving magnetic field component, as a driving magnetic field component.

Figure 7A:
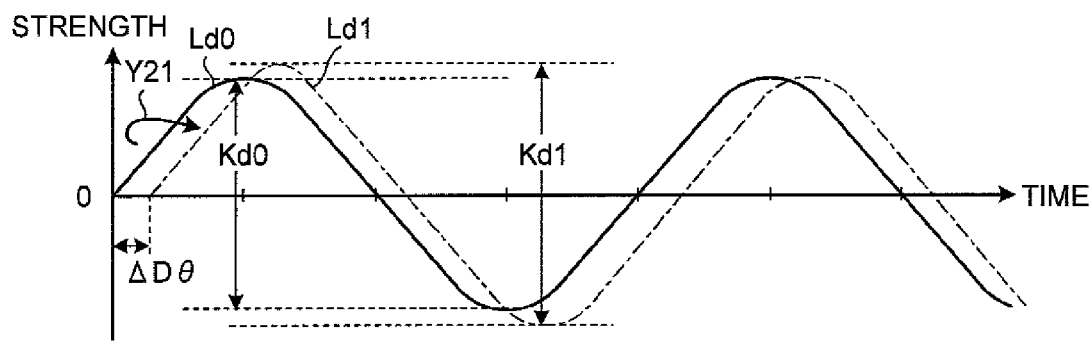
FIG. 7A is a diagram illustrating time dependence with respect to the strength of a driving magnetic field generated by a magnetic field generating coil.
Figure 7B:
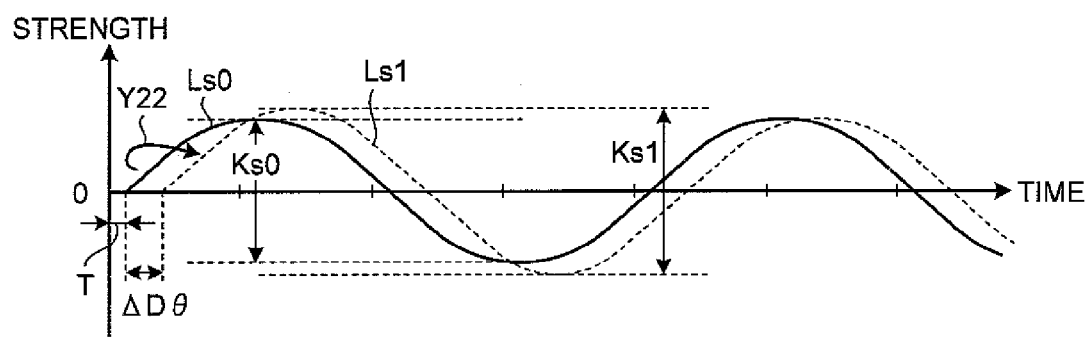
FIG. 7B is a diagram illustrating time dependence with respect to the strength of a driving magnetic field detected by a detecting coil.
Figure 7C:
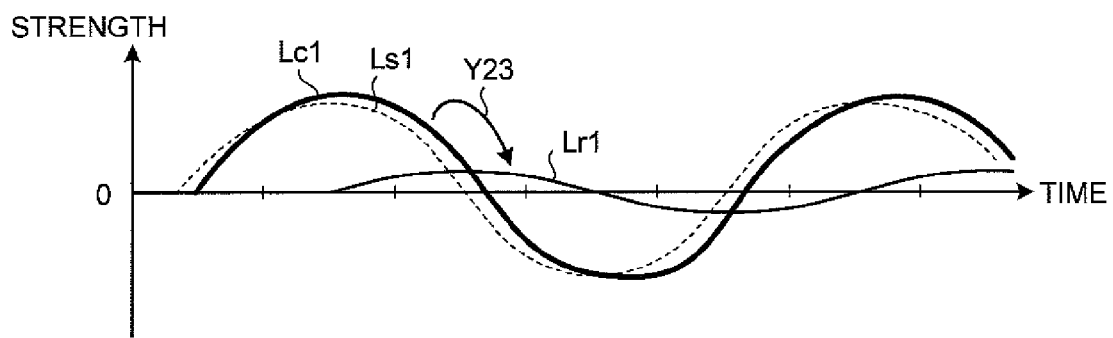
FIG. 7C is a diagram illustrating time dependence with respect to the strength of a synthetic magnetic field detected by a detecting coil.

With reference to FIG. 7, a process content of the first modification of the present first embodiment will be described. FIG. 7A is a diagram illustrating time dependence with respect to the strength of the driving magnetic field generated by the magnetic field generating coil D1. FIG. 7B is a diagram illustrating time dependence with respect to the strength of the driving magnetic field detected by the detecting coil F. FIG. 7C is a diagram illustrating time dependence with respect to the strength of the synthetic magnetic field detected by the detecting coil. FIG. 7B illustrates the detection result of the detecting coil F when the capsule endoscope 10 is not positioned in the detection range K.

As indicated by a curved line Ld0 of FIG. 7A, when the magnetic field generating coil D1 has generated a driving magnetic field at a predetermined frequency, the detecting coil F detects the driving magnetic field at the same frequency in the state in which the driving magnetic field has been shifted by time T according to the distance to the magnetic field generating coil D1 and the characteristics of the detecting coil F as indicated by a curved line Ls0 of FIG. 7B. Moreover, when the magnetic field generating coil D1 has generated a driving magnetic field with an amplitude Kd0, the detecting coil F detects a driving magnetic field with an amplitude Ks0. The ratio of the amplitude Kd0 of the driving magnetic field generated by the magnetic field generating coil D1 and the amplitude Ks0 of the driving magnetic field detected by the detecting coil F is determined by the characteristics of the magnetic field generating coil D1, the characteristics of the detecting coil F, and relative position relation between the magnetic field generating coil D1 and the detecting coil F. Thus, when the driving magnetic field generated by the magnetic field generating coil D1 is generated with a phase, which is shifted by ΔDθ due to a time-dependent change as indicated by an arrow Y21 as compared with the curved line Ld0, as indicated by a curved line Ld1 of FIG. 7A, and the amplitude thereof is changed from Kd0 to Kd1, the driving magnetic field detected by the detecting coil F has a phase, which is shifted by ΔDθ as indicated by an arrow Y22 as compared with the curved line Ls0, as indicated by a curved line Ls1 of FIG. 7B, and an amplitude of Ks1 is obtained by multiplying Ks0 by (Kd1/Kd0).

Consequently, when obtaining a degree, by which the phase of the driving magnetic field actually generated by the magnetic field generating coil D1 is changed from the phase of a driving magnetic field serving as a reference, in order to detect the position of the capsule endoscope 10, and a degree, by which the amplitude of the driving magnetic field actually generated by the magnetic field generating coil D1 is changed from the amplitude of the driving magnetic field serving as a reference, in order to detect the position of the capsule endoscope 10, it is possible to obtain the phase and amplitude of a component corresponding to the driving magnetic field of the synthetic magnetic field detected by the detecting coil F. The phase and amplitude of one driving magnetic field component of the synthetic magnetic field detected by the detecting coil F are obtained, so that a driving magnetic field component indicated by a curved line Ls1 is separated from a synthetic magnetic field indicated by a curved line Lc1 of FIG. 7C, resulting in the acquirement of a resonant magnetic field component, which is generated by the capsule endoscope 10 indicated by a curved line Lr1, as indicated by an arrow Y23.

Meanwhile, the phase of the driving magnetic field in the magnetic field generating coil D1 is the same as the phase of the current flowing through the magnetic field generating coil D1, and a constant proportional relation is established between the amplitude of the driving magnetic field in the magnetic field generating coil D1 and the amplitude of the current flowing through the magnetic field generating coil D1. Therefore, in the first modification according to the first embodiment, the current detecting unit 32 detects the driving current flowing through the magnetic field generating coil D1 at the time of position detection, obtains the amplitude of the driving current, obtains a ratio of the obtained amplitude with respect to the amplitude of the reference current value, and multiplies the obtained ratio of the amplitude of the driving current by the amplitude of the reference voltage value, thereby acquiring the amplitude of the driving magnetic field component detected by each detecting coil F.

Specifically, similarly to the first embodiment, in the first modification according to the first embodiment, when the capsule endoscope 10 is not positioned in the detection space K, the detection value of the magnetic field detected by the detecting coil F and the detection value of the driving current detected by the current detecting unit 32 are used as the reference values. Then, the calibration calculating unit 51 calculates the amplitude and phase of a driving magnetic field component based on the detection value of the driving current detected by the current detecting unit 32 during the detection of the position of the capsule endoscope 10, and the reference value stored in the memory 52. Similarly to the first embodiment, the calibration calculating unit 51 obtains a phase difference between the detection value of the driving current stored in the memory 52 as the reference value and the detection value of the driving current, which actually flows through the magnetic field generating coil D1 and is detected by the current detecting unit 32, thereby calculating the phase of the driving magnetic field component. Moreover, the calibration calculating unit 51 obtains the amplitude ratio of the detection value of the driving current stored in the memory 52 as the reference value and the detection value of the driving current which actually flows through the magnetic field generating coil D1 and is detected by the current detecting unit 32. Then, the calibration calculating unit 51 calculates a value obtained by multiplying the obtained amplitude ratio by the amplitude of the driving magnetic field component stored as the reference value, and outputs the value to the position information calculating unit 53 as the amplitude of the driving magnetic field component of the driving magnetic field actually generated by the magnetic field generating coil D1.

Figure 8:
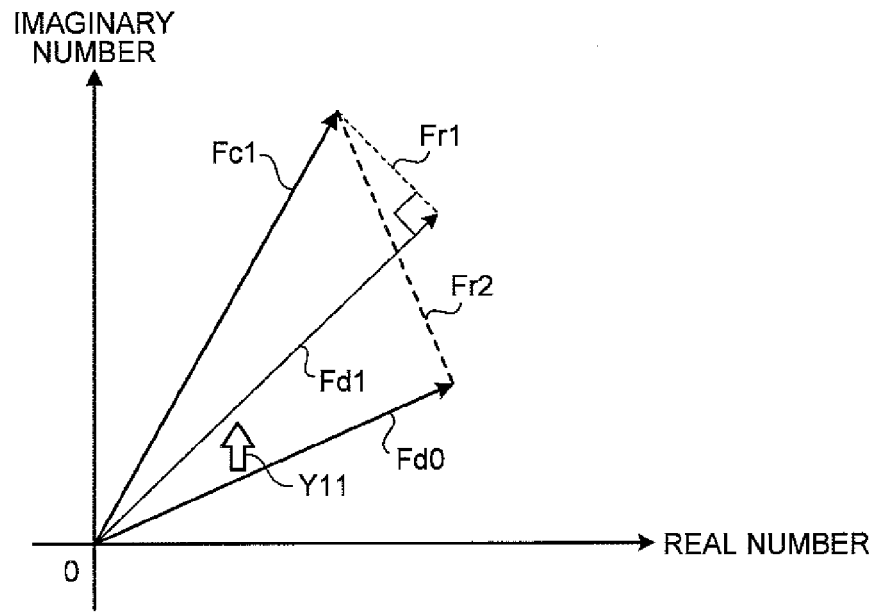
FIG. 8 is a diagram illustrating the relation among a driving magnetic field by the magnetic field generating coil illustrated in FIG. 1, a synthetic magnetic field which is a magnetic field detected by a detecting coil, and a resonant magnetic field of a capsule endoscope.

Then, as illustrated in FIG. 8, the position information calculating unit 53 subtracts the driving magnetic field Fd1 obtained based on the amplitude and phase output by the calibration calculating unit 51 from the synthetic magnetic field Fc1 detected by the detecting coil F, thereby obtaining the resonant magnetic field Fr1 generated by the capsule endoscope 10. Then, the position information calculating unit 53 performs a predetermined calculation process with respect to the resonant magnetic field Fr1, thereby deriving the current position or direction of the capsule endoscope 10.

Conventionally, in the state in which the capsule endoscope 10 is not introduced into the detection space K, the magnetic field generating coil D1 is driven to form a driving magnetic field in the detection space K, the driving magnetic field Fd0 detected by the detecting coil F is obtained in advance in such a state, and the driving magnetic field Fd0 is used as a driving magnetic field to be subtracted from the synthetic magnetic field Fc1. However, in the conventional method, even when the driving magnetic field actually generated from the magnetic field generating coil D1 is changed into the driving magnetic field Fd1 with a phase and an amplitude, which are different from those of the driving magnetic field Fd0 as indicated by the arrow Y11 due to a time-dependent change of the magnetic field generating unit, a temperature change, and interference with an LC resonant circuit, the driving magnetic field Fd0 is used as a driving magnetic field to be subtracted from the synthetic magnetic field Fc. Therefore, in the conventional method, since a change in the driving magnetic field is not reflected in the separation process of the resonant magnetic field and position detection is performed using a magnetic field Fr2 different from the actual resonant magnetic field Fr1, resulting in the deterioration of position detection accuracy.

On the other hand, in the first modification of the first embodiment, other than the driving magnetic field Fd0 before being changed, since the position detection is performed after the phase and amplitude of the driving magnetic field actually generated by the magnetic field generating coil D1 are obtained based on the driving current which flows through the magnetic field generating coil D1 and is detected by the current detecting unit 32, it is possible to correctly separate the resonant magnetic field Fr1 from the synthetic magnetic field Fc1, thereby achieving the same effect as the first embodiment. Furthermore, even in the first modification of the first embodiment, during the position detection, since the driving magnetic field component is obtained using the detection value of the current detecting unit 32 and the reference value, it is possible to achieve an accurate position detection result excluding the individual difference of the position detecting system 1 and the influence of the peripheral environment of the position detecting system 1.

Figure 9:
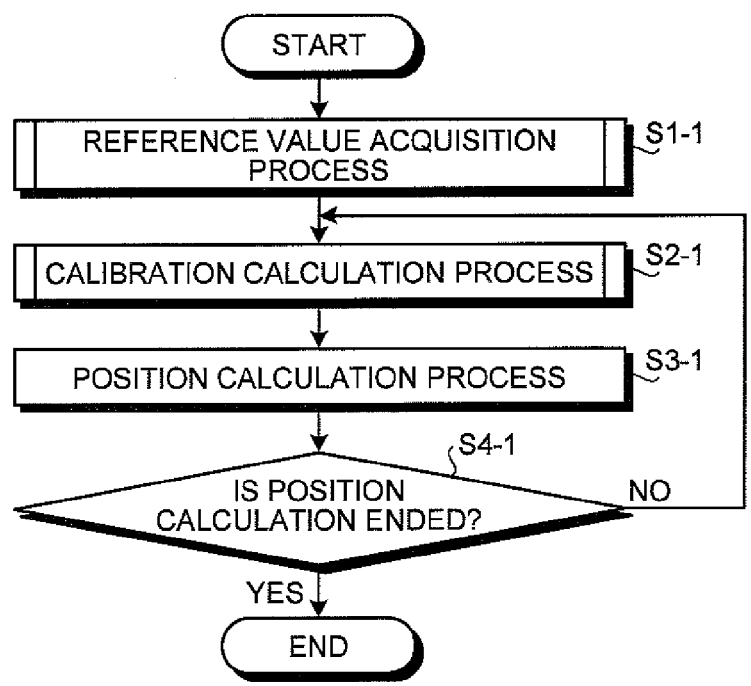
FIG. 9 is a flowchart illustrating the procedure of a position detection process according to a first modification of the first embodiment.

Next, with referenced to FIG. 9, the position detection process in the first modification of the first embodiment will be described. FIG. 9 is a flowchart illustrating the procedure of the position detection process in the first modification of the first embodiment.

As illustrated in FIG. 9, in the first modification of the first embodiment, a reference value acquisition process is performed to acquire a detection value of the driving magnetic field detected by each detecting coil F and a detection value of a driving current detected by the current detecting unit 32 as reference values in the case in which the capsule endoscope 10 is not positioned in the detection space K (step S1-1). The reference value acquisition process is not necessary to be performed for each position detection, but is only necessary to be performed when the position detecting system 1 is installed, and parts of the magnetic field generating coil D1 and the detecting coil F are exchanged. Furthermore, the reference value acquisition process may be periodically performed in order to hold constant accuracy.

Then, in the first modification of the first embodiment, a position detection process is performed to detect the position of the capsule endoscope 10 in the state in which the capsule endoscope 10 is actually disposed in the detection space K. In such a case, in the position detecting system 1, the calibration calculating unit 51 performs a calibration calculation process of calculating the amplitude and the phase of a driving magnetic field component of a synthetic magnetic field detected by each detecting coil F (step S2-1). Then, the position information calculating unit 53 performs a position calculation process of obtaining a difference between the synthetic magnetic field detected by the detecting coil F and the driving magnetic field, based on the amplitude and the phase of the driving magnetic field component, which are calculated by the calibration calculating unit 51 from the synthetic magnetic field detected by the detecting coil F, and operating the position and direction of the capsule endoscope 10 using the obtained difference as a resonant magnetic field by the capsule endoscope 10 (step S3-1). The calculating result of the position and direction by the position information calculating unit 53 is output to the control unit 21 and output to the display unit 24 under the control of the control unit 21.

Then, similarly to step S4 illustrated in FIG. 4, the control unit 21 determines whether the position detection process has been completed based on an instruction input from the operation input unit 23 (step S4-1). When it is determined that the position detection process has not been completed (step S4-1: No), the control unit 21 returns to step S2-1 in order to continue the position detection, and performs the calibration calculation process. Meanwhile, when it is determined that the position detection process has been completed (step S4-1: Yes), the control unit 21 also completes a control process for the magnetic field generating coil D1, the detecting coil F, the converter 40, and the position detecting unit 50, together with the completion of the position detection.

Figure 10:
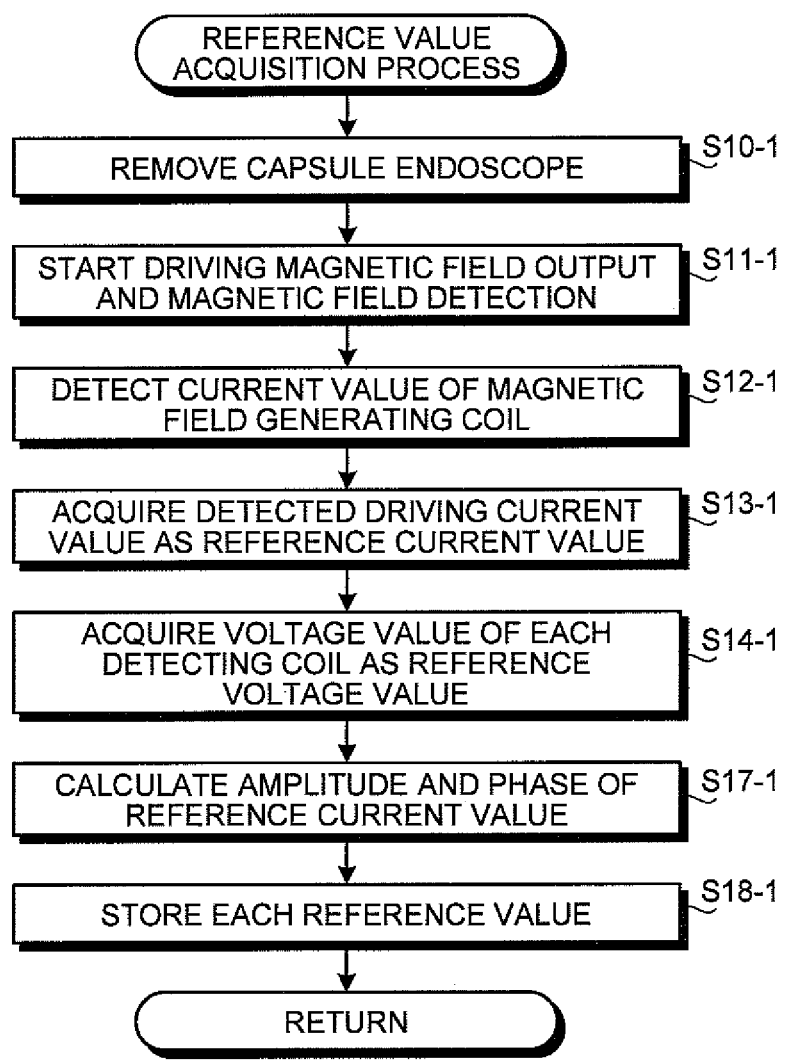
FIG. 10 is a flowchart illustrating the procedure of a reference value acquisition process illustrated in FIG. 9.

Next, the reference value acquisition process illustrated in FIG. 9 will be described. FIG. 10 is a flowchart illustrating the procedure of the reference value acquisition process illustrated in FIG. 9. As illustrated in FIG. 10, in the reference value acquisition process, the capsule endoscope 10 (detected object) is taken out of the detection space K (step S10-1), and a driving magnetic field output process by the magnetic field generating coil D1 and magnetic field detection by the detecting coil F are started (step S11-1), similarly to step S10 and step S11 of FIG. 5.

Then, similarly to step S12 of FIG. 5, the current detecting unit 32 detects a current value of a driving current flowing through the magnetic field generating coil D1 in synchronization with the magnetic field detection by each detecting coil F (step S12-1). Similarly to the first embodiment, the driving current value detected by the current detecting unit 32 is acquired in the calibration calculating unit 51 as a reference current value after a predetermined frequency component is separated by the converter 40 (step S13-1). Meanwhile, in the same manner, each voltage value corresponding to the magnetic field detected by each detecting coil F is also acquired in the calibration calculating unit 51 as a reference voltage value corresponding to each detecting coil F after a predetermined frequency component is separated by the converter 40 (step S14-1).

Then, the calibration calculating unit 51 calculates the amplitude and the phase of a reference current value based on a real number value and an imaginary number value of the obtained reference current value (step S17-1). The calibration calculating unit 51 stores the reference current value, each reference voltage value, and the amplitude and the phase of the calculated reference current value in the memory 52 as reference values (step S18-1), and completes the reference value acquisition process.

Figure 11:
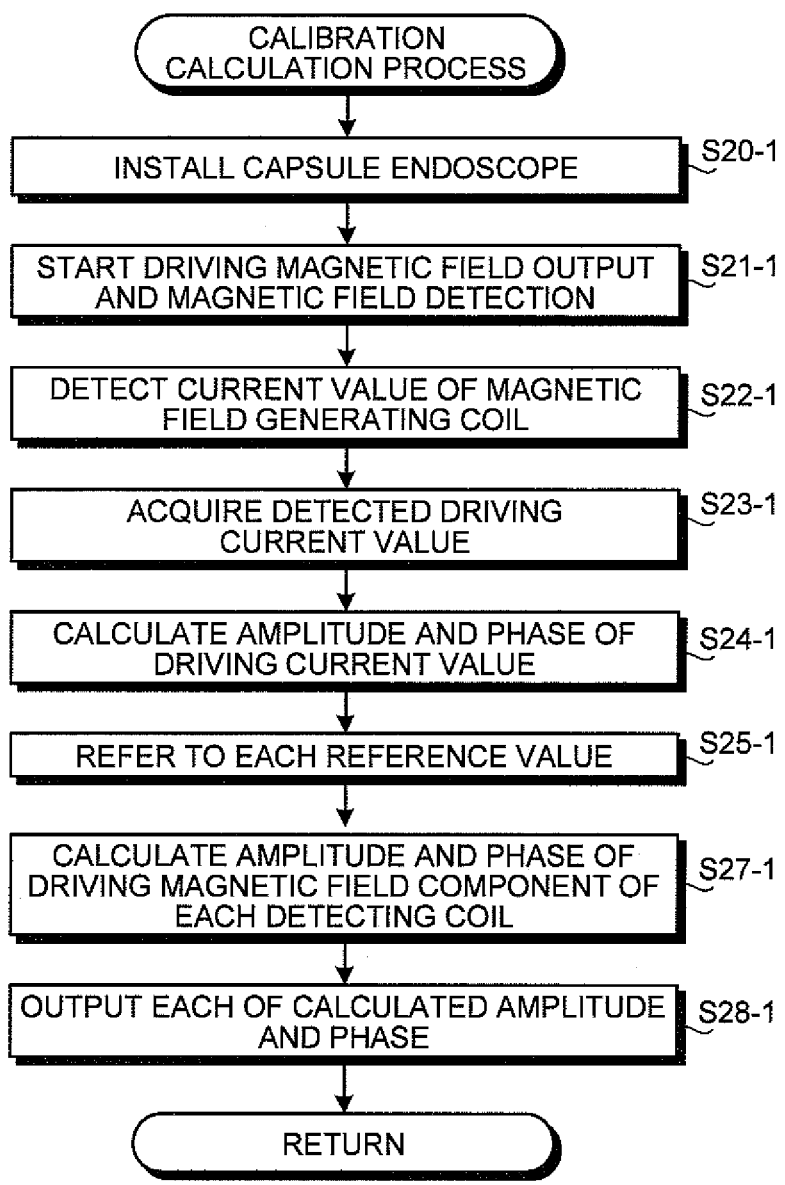
FIG. 11 is a flowchart illustrating the procedure of a calibration calculation process illustrated in FIG. 9.

Next, the calibration calculation process illustrated in FIG. 9 will be described. FIG. 11 is a flowchart illustrating the procedure of the calibration calculation process illustrated in FIG. 9. As illustrated in FIG. 11, in the calibration calculation process, similarly to step S20 and step S21 of FIG. 6, in order to start a position detection process, the capsule endoscope 10 (detected object) is installed in the detection space K (step S20-1), and the driving magnetic field output process by the magnetic field generating coil D1 and the magnetic field detection by each detecting coil F are started (step S21-1). The voltage value corresponding to the magnetic field detected by each detecting coil F is output to the position information calculating unit 53 as the synthetic magnetic field detected by each detecting coil F after the voltage value is separated to a predetermined frequency component used in the position detection in the converter 40.

Then, similarly to step S22 of FIG. 6, the current detecting unit 32 detects the current value of the driving current flowing through the magnetic field generating coil D1, in synchronization with the magnetic field detection of each detecting coil F (step S22-1). Similarly to step S23 of FIG. 6, the driving current value detected by the current detecting unit 32 is acquired in the calibration calculating unit 51 as a driving current value after a predetermined frequency component is separated in the converter 40 (step S23-1).

Next, the calibration calculating unit 51 calculates the amplitude and phase of the driving current value (step S24-1). Then, the calibration calculating unit 51 refers to each reference value in the memory 52 (step S25-1).

The calibration calculating unit 51 calculates the amplitudes and the phases of the driving magnetic field components of the synthetic magnetic field, which is detected by each detecting coil F, based on the amplitude and the phase of the calculated driving current value and the referred each reference value (step S27-1). Then, the calibration calculating unit 51 outputs the calculated amplitudes and phases, that is, the amplitudes and the phases of the driving magnetic field components of the synthetic magnetic field detected by each detecting coil F to the position information calculating unit 53 (step S28-1). The position information calculating unit 53 performs a separation process, which separates a resonant magnetic field by subtracting a driving magnetic field corresponding to the amplitude and the phase of the driving magnetic field component output from the calibration calculating unit 51, from the synthetic magnetic field, for each detection result by each detecting coil F, and performs a predetermined calculation process with respect to the separated resonant magnetic field, thereby deriving the current position or direction of the capsule endoscope 10.

Next, the calculation processes of step S27-1 and step S28-1 will be described using the detecting coil F1 of the detecting coils F as an example. In addition, the phase of the reference current value stored in the memory 52 is set as Dθ, the amplitude of the reference current value is set as DX, a real number value of the reference voltage value in the detecting coil F1 is set as SR1, an imaginary number value of the reference voltage value in the reference coil F1 is set as SI1, the phase of the driving current value detected by the current detecting unit 32 is set as Dθ', and the amplitude of the driving current value is set as DX'.

Similarly to the first embodiment, the calibration calculating unit 51 calculates the phase difference ΔDθ between the reference current value and the driving current value by using Equation (1) above. Next, the calibration calculating unit 51 calculates the ratio Kx of the amplitude of the reference current value and the amplitude of the driving current value by using Equation (4) below.

$$DX'/DX=Kx \quad (4)$$

Next, the calibration calculating unit 51 calculates a real number value SR1' and an imaginary number value SI1' of a driving voltage value, which corresponds to the driving magnetic field component of the synthetic magnetic field detected by the detecting coil F1, by using the phase difference ΔDθ obtained by Equation (1), the amplitude ratio Kx obtained by Equation (4), and the reference voltage value. Specifically, by means of Equation (5) and Equation (6) below, the phase of each reference voltage value is added to each value of the reference voltage value by ΔDθ and is multiplied by the amplitude ratio Kx, thereby calculating the real number value SR1' and the imaginary number value SI1' of the driving voltage value.

$$SR1'=Kx \times (SR1 \times \cos \Delta\theta - SI1 \times \sin \Delta\theta) \quad (5)$$

$$SI1'=Kx \times (SR1 \times \sin \Delta\theta + SI1 \times \cos \Delta\theta) \quad (6)$$

Then, the calibration calculating unit 51 calculates the amplitude and the phase of the driving voltage value in the detecting coil F1 based on the real number value DR1' and the imaginary number value DI1' of the driving voltage value, which are calculated using Equation (5) and Equation (6). In the same manner, for the detecting coils F2 to F8, the calibration calculating unit 51 calculates the amplitude and the phase of each driving voltage value in the detecting coils F2 to F8.

As described above, in the first modification of the first embodiment, the procedures illustrated in FIGS. 9 to 11 are performed, the amplitude and the phase of a driving magnetic field component for a driving magnetic field, which is actually generated by the magnetic field generating coil D1, are obtained as a driving magnetic field component constituting the synthetic magnetic field detected by each detecting coil F, and the resonant magnetic field generated by the capsule endoscope 10 is accurately separated from the synthetic magnetic field based on the amplitude and the phase of the obtained driving magnetic field component, thereby accurately detecting the position of the capsule endoscope 10.

Second Modification According to First Embodiment

Next, a second modification of the first embodiment will be described. In the second modification of the first embodiment, other than a reference value, a real number value and an imaginary number value of the driving magnetic field component are calculated by simulation using the characteristics of a magnetic field generating coil prepared in advance, the characteristics of each magnetic field detecting coil, and relative position information between the magnetic field generating coil and the magnetic field detecting coil.

Figure 12:
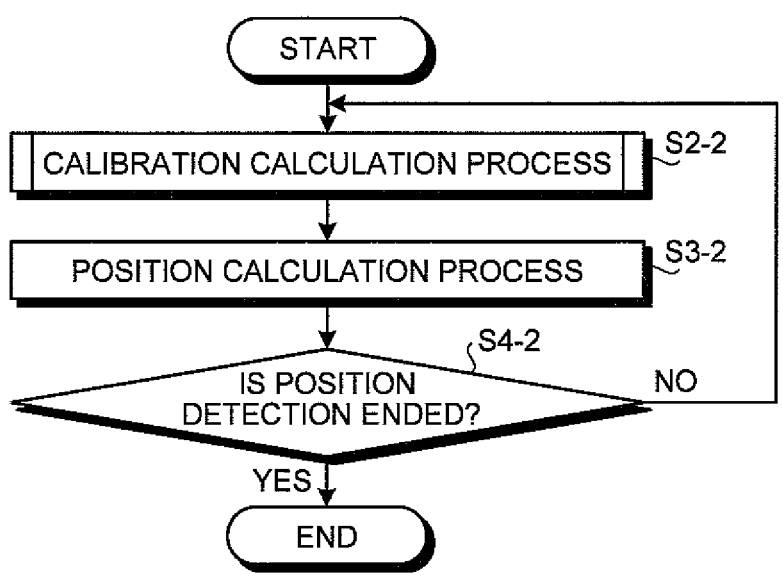
FIG. 12 is a flowchart illustrating the procedure of a position detection process according to a second modification of the first embodiment.

With reference to FIG. 12, a position detection process in the second modification of the first embodiment will be described. FIG. 12 is a flowchart illustrating the procedure of the position detection process according to the second modification of the first embodiment.

As illustrated in FIG. 12, in the second modification of the first embodiment, the reference value acquisition processes illustrated in FIG. 4 and FIG. 9 are deleted, and a calibration calculation process (step S2-2) by the calibration calculating unit 51, a position calculation process by the position information calculating unit 53 (step S3-2), and a position detection completion determination process (step S4-2) by the control unit 21 are performed. In addition, when it is determined that a position detection process has not been completed (step S4-2: No), the control unit 21 returns to step S2-2 in order to continue the position detection, and performs the calibration calculation process. Meanwhile, when it is determined that the position detection process has been completed (step S4-2: Yes), the control unit 21 also completes a control process for the magnetic field generating coil D1, the detecting coil F, the converter 40, and the position detecting unit 50, together with the completion of the position detection.

Figure 13:
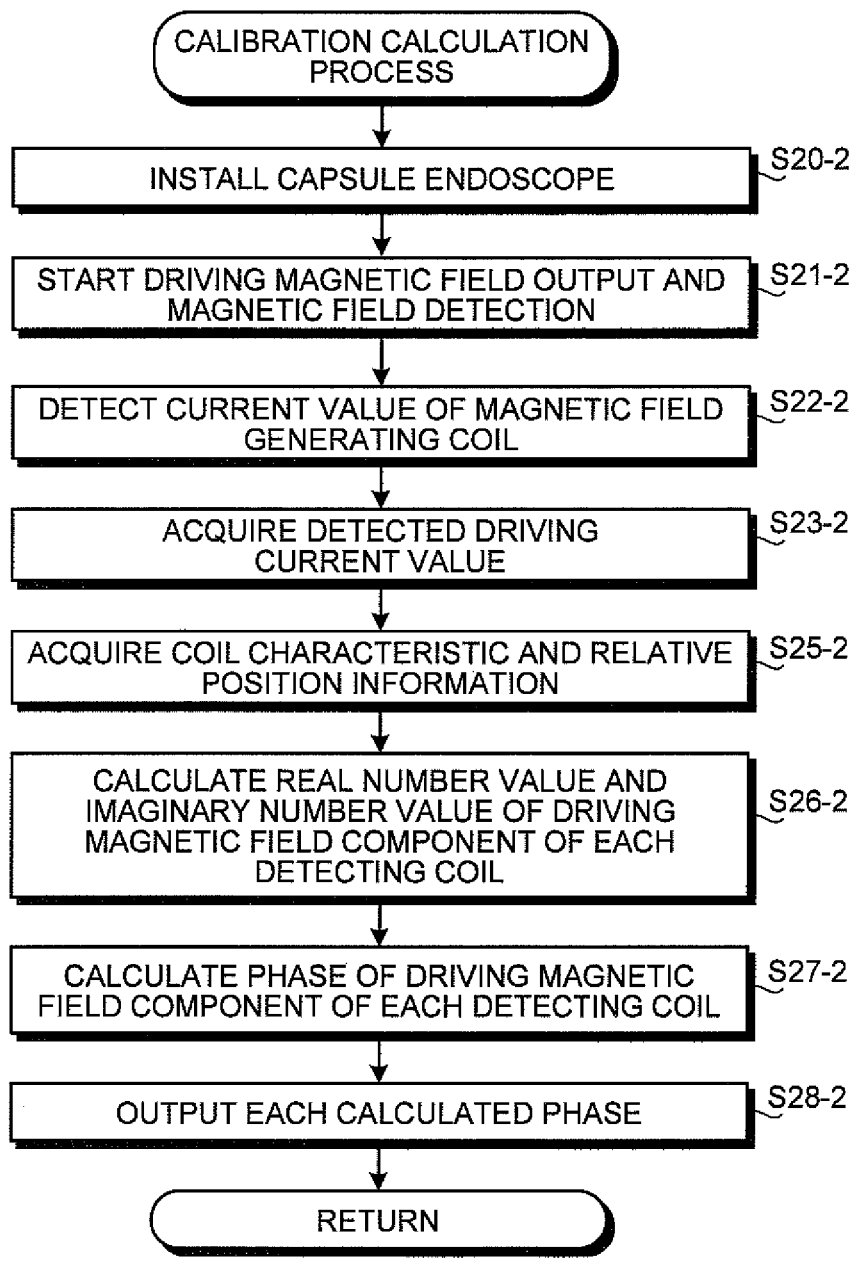
FIG. 13 is a flowchart illustrating the procedure of a calibration calculation process illustrated in FIG. 12.

Next, the calibration calculation process illustrated in FIG. 12 will be described. FIG. 13 is a flowchart illustrating the procedure of the calibration calculation process illustrated in FIG. 12. As illustrated in FIG. 12, in the calibration calculation process, similarly to step S20 and step S21 of FIG. 6, in order to start a position detection process, the capsule endoscope 10 (detected object) is installed in the detection space K (step S20-2), and the driving magnetic field output process by the magnetic field generating coil D1 and the magnetic field detection by each detecting coil F are started (step S21-2). The voltage value corresponding to the magnetic field detected by each detecting coil F is output to the position information calculating unit 53 as the synthetic magnetic field detected by each detecting coil F after the voltage value is separated to a predetermined frequency component used in the position detection in the converter 40.

Then, similarly to step S22 of FIG. 6, the current detecting unit 32 detects the current value of the driving current flowing through the magnetic field generating coil D1, in synchronization with the magnetic field detection of each magnetic field detecting coil F (step S22-2). Similarly to step S23 of FIG. 6, the driving current value detected by the current detecting unit 32 is acquired in the calibration calculating unit 51 as a driving current value after a predetermined frequency component is separated in the converter 40 (step S23-2).

Next, the calibration calculating unit 51 acquires the characteristics of the magnetic field generating coil D1, the characteristics of each detecting coil F, and each piece of relative position information between the magnetic field generating coil D1 and the magnetic field detecting coils F (step S25-2). This information is obtained in advance and, for example, is stored in the memory 52. Then, the calibration calculating unit 51 calculates a real number value and an imaginary number value of a driving magnetic field component in each detecting coil F by simulation based on the characteristics of the magnetic field generating coil D1, the characteristics of each magnetic field detecting coil F, each piece of relative position information between the magnetic field generating coil D1 and the magnetic field detecting coils F, and the driving current value which are acquired (step S26-2).

Then, the calibration calculating unit 51 calculates the phase of the driving magnetic field component in each detecting coil F based on the calculated real number value and the imaginary number value of the driving magnetic field component in each detecting coil F (step S27-2). In addition, the calibration calculating unit 51 may also calculate the phase and the amplitude of driving magnetic field component in each detecting coil F in step S27-2. Then, the calibration calculating unit 51 outputs each calculated phase of the driving magnetic field component of the synthetic magnetic field detected by each detecting coil F to the position information calculating unit 53 (step S28-2). The position information calculating unit 53 separates a resonant magnetic field from the synthetic magnetic field detected by each detecting coil F by using the phase of the driving magnetic field component output from the calibration calculating unit 51, or the amplitude and the phase of the driving magnetic field component output from the calibration calculating unit 51, and performs a predetermined calculation process with respect to the separated resonant magnetic field, thereby deriving the current position or direction of the capsule endoscope 10.

As described above, even when the driving magnetic field component actually generated by the magnetic field generating coil D1 is obtained by simulation, the resonant magnetic field generated by the capsule endoscope 10 can be accurately separated from the synthetic magnetic field, so that the position of the capsule endoscope 10 can be accurately detected.

Third Modification According to First Embodiment

Next, a third modification of the first embodiment will be described. In the third modification of the first embodiment, an LUT (look-up table) is created in advance, in which detection values of detecting coils for each phase of a driving magnetic field by a magnetic field generating coil are made correspond to detection values of a current detecting unit, and a driving magnetic field component of a synthetic magnetic field is obtained with reference to the LUT at the time of position detection.

In such a case, the control unit 21 allows the magnetic field generating coil D1 to generate driving magnetic fields with different phases and each detecting coil and the current detecting unit 32 to perform a detection process. Then, the control unit 21 acquires each detection value of the magnetic field, which is detected by each detecting coil F, and each detection value of a driving current, which is detected by the current detecting unit 32, for each phase of the driving magnetic field generated by the magnetic field generating coil D1. The memory 52 stores an LUT representing a correspondence relation in which each acquired detection value of the magnetic field, which is detected by each detecting coil F, is made correspond to each detection value of the driving current, which is detected by the current detecting unit 32, for each phase of the driving magnetic field generated by the magnetic field generating coil D1. Moreover, the calibration calculating unit 51 calculates the phase of a driving magnetic field component, which corresponds to the driving magnetic field of the synthetic magnetic field detected by each detecting coil F, based on the detection value of the driving current detected by the current detecting unit 32, and the LUT stored in the memory 52 during a position detection process.

Figure 14:
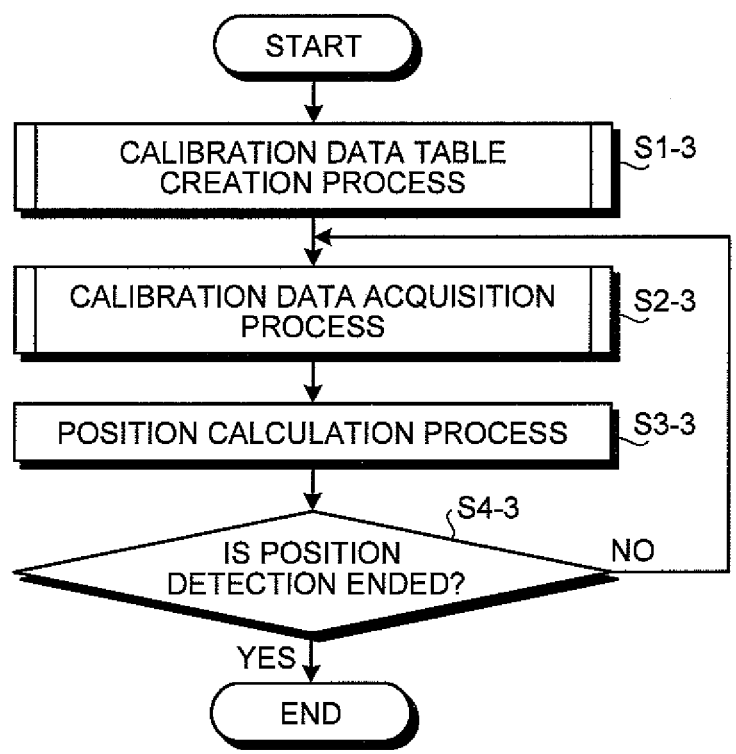
FIG. 14 is a flowchart illustrating the procedure of a position detection process according to a third modification of the first embodiment.

With reference to FIG. 14, the position detection process in the third modification of the first embodiment will be described. FIG. 14 is a flowchart illustrating the procedure of the position detection process according to the third modification of the first embodiment.

As illustrated in FIG. 14, in the third modification of the first embodiment, instead of the reference value acquisition processes illustrated in FIGS. 4 to 9, a calibration data table creation process (step S1-3) is performed. In the calibration data table creation process, the LUT is created in which the detection values of the detecting coils for each phase of the driving magnetic field by the magnetic field generating coil are made correspond to the detection values of the current detecting unit. Next, the calibration calculating unit 51 performs a calibration data acquisition process of calculating the phase of the driving magnetic field component corresponding to the driving magnetic field of the synthetic magnetic field detected by each detecting coil F based on the detection value of the driving current detected by the current detecting unit 32, and the LUT stored in the memory 52 (step S2-3). Then, similarly to step S3 and step S4 illustrated in FIG. 4, a position calculation process by the position information calculating unit 53 (step S3-3), and a position detection completion determination process (step S4-3) by the control unit 21 are performed. In addition, when it is determined that a position detection process has not been completed (step S4-3: No), the control unit 21 returns to step S2-3 in order to continue the position detection, and performs the calibration data acquisition process. Meanwhile, when it is determined that the position detection process has been completed (step S4-3: Yes), the control unit 21 also completes a control process for the magnetic field generating coil D1, the detecting coil F, the converter 40, and the position detecting unit 50, together with the completion of the position detection.

Figure 15:
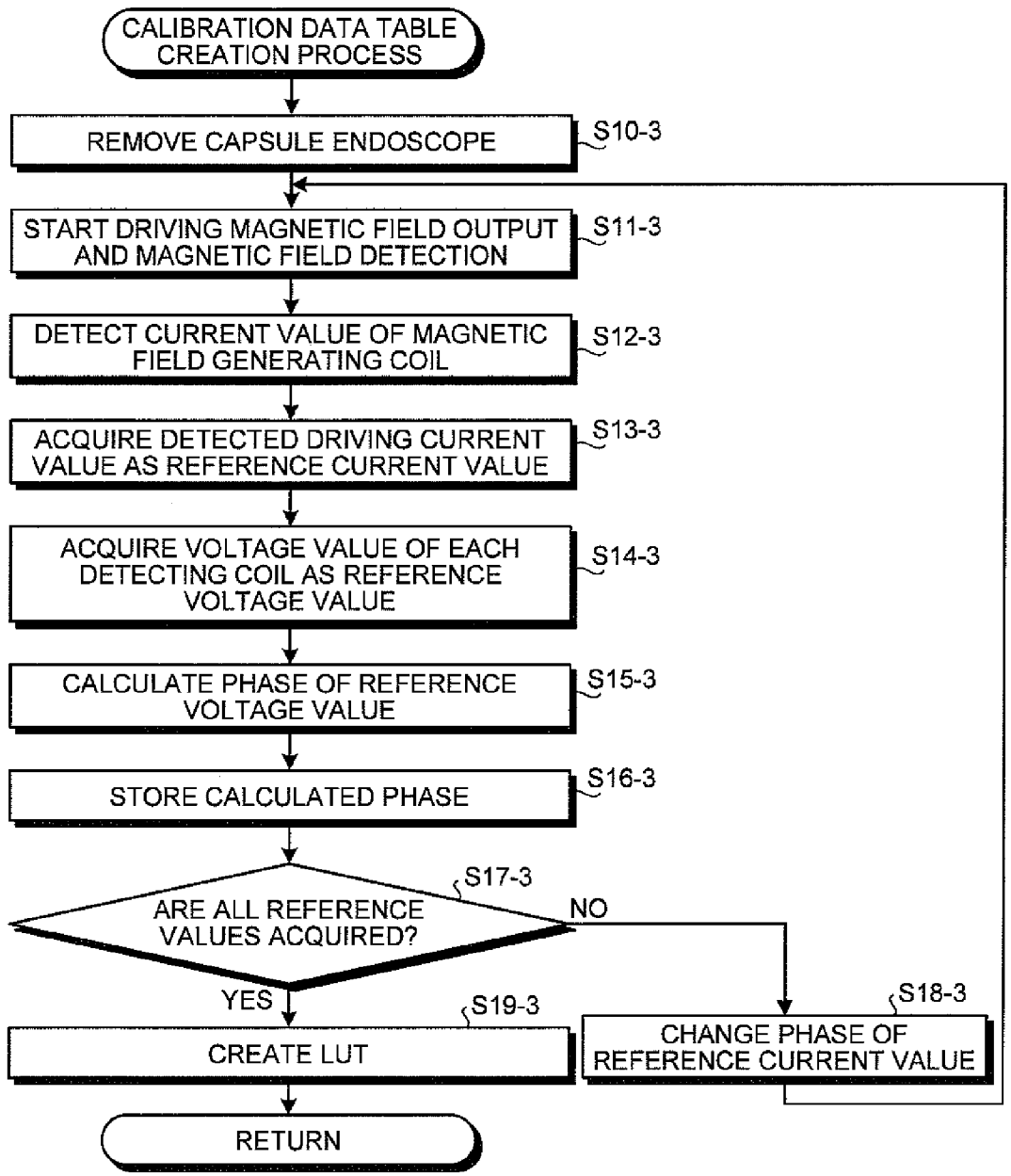
FIG. 15 is a flowchart illustrating the procedure of a calibration data table creation process illustrated in FIG. 14.

Next, the calibration data table creation process illustrated in FIG. 14 will be described. FIG. 15 is a flowchart illustrating the procedure of the calibration data table creation process illustrated in FIG. 14.

As illustrated in FIG. 15, the capsule endoscope 10 (detected object) is taken out of the detection space K (step S10-3). Next, driving magnetic field output by the magnetic field generating coil D1 and magnetic field detection by the detecting coil F are started (step S11-3). First, the magnetic field generating coil D1 generates a driving magnetic field under predetermined initial conditions. Similarly to step S12 of FIG. 5, the current detecting unit 32 detects a current value of a driving current flowing through the magnetic field generating coil D1 in synchronization with the magnetic field detection by each detecting coil F (step S12-3). Similarly to the first embodiment, the driving current value detected by the current detecting unit 32 is acquired in the calibration calculating unit 51 as a reference current value corresponding to the phase of the driving magnetic field generated by the magnetic field generating coil D1 after a predetermined frequency component is separated by the converter 40 (step S13-3). Meanwhile, in the same manner, each voltage value corresponding to the magnetic field detected by each detecting coil F is also acquired in the calibration calculating unit 51 as a reference voltage value corresponding to each detecting coil F and a reference voltage value corresponding to the phase of the driving magnetic field generated by the magnetic field generating coil D1 after a predetermined frequency component is separated by the converter 40 (step S14-3).

The calibration calculating unit 51 calculates the phase of the acquired reference voltage value as the phase of a driving magnetic field corresponding to the acquired reference current value (step S15-3). The calibration calculating unit 51 stores the phase of the reference voltage value calculated as the phase of the driving magnetic field by allowing the phase of the reference voltage value to correspond to the reference current value (step S16-3).

Then, the control unit 21 determines whether all reference values have been acquired for all phases of acquisition targets (step S17-3). When it is determined that all reference values have not been acquired for all phases of the acquisition targets (step S17-3: No), the control unit 21 changes the phase of the driving current value flowing through the magnetic field generating coil D1 to the phase of a reference current value which is the next acquisition target (step S18-3). Then, the procedure returns to step S11-3, and the magnetic field generating coil D1 generates a driving magnetic field such that the phase of the driving current flowing through the magnetic field generating coil D1 is the same as the changed phase, and the detecting coil F also starts magnetic field detection (step S11-3). Thereafter, the position detecting system 1 performs the processes illustrated in step S12-3 to step S16-3, obtains the phases of a reference current value and a reference voltage value corresponding to the changed phase, and stores the phase of the reference voltage value as the phase of the driving magnetic field by allowing the phase of the reference voltage value to correspond to the phase of the reference current value.

On the other hand, when the control unit 21 determines that all reference values have been acquired for all phases of the acquisition targets (step S17-3: Yes), the calibration calculating unit 51 creates an LUT in which each phase of the driving magnetic field is made correspond to the detection values of the current detecting unit 32 (step S19-3), and stores the LUT in the memory 52. In the LUT, the reference current value is made correspond to each phase of the driving magnetic field.

Figure 16:
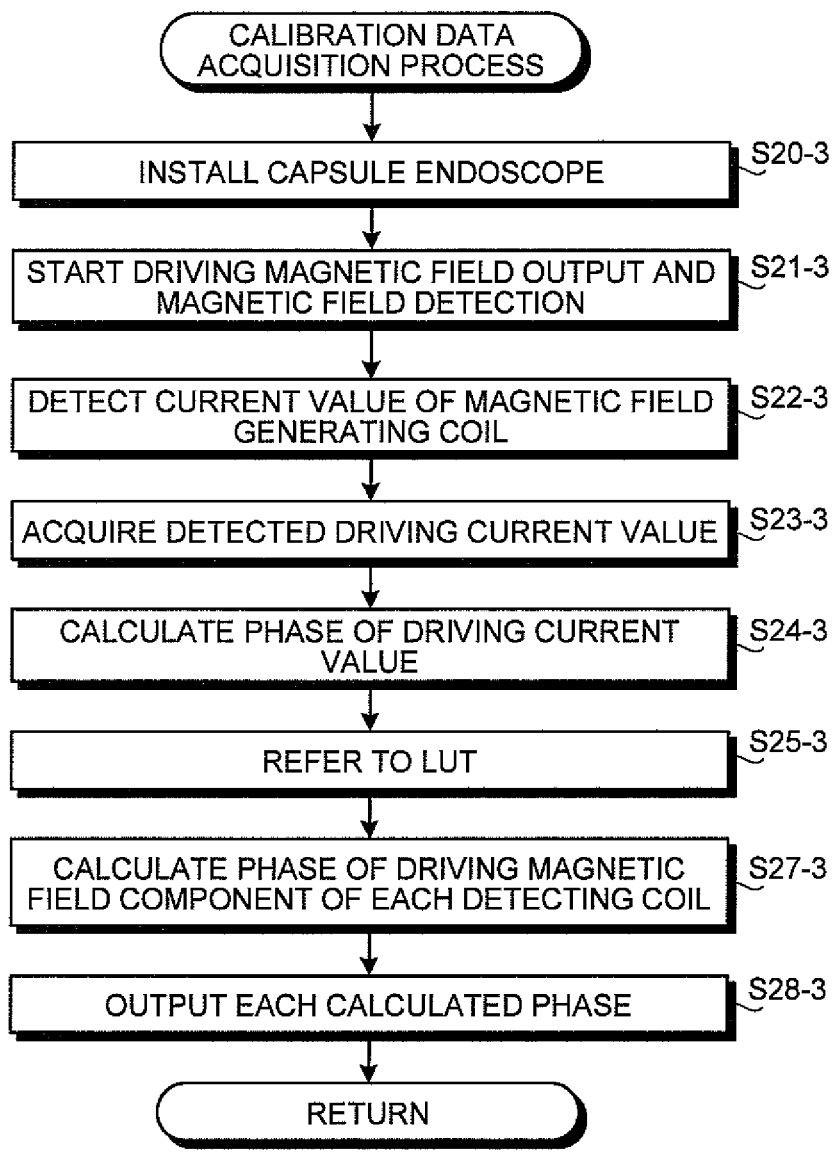
FIG. 16 is a flowchart illustrating the procedure of a calibration data acquisition process illustrated in FIG. 14.

Next, the calibration data acquisition process illustrated in FIG. 14 will be described. FIG. 16 is a flowchart illustrating the procedure of the calibration data acquisition process illustrated in FIG. 14.

As illustrated in FIG. 16, in the calibration data acquisition process, similarly to step S20 and step S21 of FIG. 6, in order to start a position detection process, the capsule endoscope 10 (detected object) is installed in the detection space K (step S20-3), and the driving magnetic field output process by the magnetic field generating coil D1 and the magnetic field detection by each detecting coil F are started (step S21-3). The voltage value corresponding to the magnetic field detected by each detecting coil F is output to the position information calculating unit 53 as the synthetic magnetic field detected by each detecting coil F after the voltage value is separated to a predetermined frequency component used in the position detection in the converter 40.

Then, similarly to step S22 of FIG. 6, the current detecting unit 32 detects the current value of the driving current flowing through the magnetic field generating coil D1, in synchronization with the magnetic field detection of each detecting coil F (step S22-3). Similarly to step S23 of FIG. 6, the driving current value detected by the current detecting unit 32 is acquired in the calibration calculating unit 51 as a driving current value after a predetermined frequency component is separated in the converter 40 (step S23-3). Similarly to step S24 illustrated in FIG. 6, the calibration calculating unit 51 calculates the phase of the driving current value (step S24-3).

Next, the calibration calculating unit 51 refers to the LUT in the memory 52 (step S25-3). The calibration calculating unit 51 acquires the phase of the driving magnetic field component of each detecting coil F corresponding to the calculated phase of the driving current value from the referred LUT (step S27-3). The calibration calculating unit 51 outputs the acquired each phase to the position information calculating unit 53 as each phase of the driving magnetic field component of the synthetic magnetic field detected by each detecting coil F (step S28-3) and completes the calibration data acquisition process. The position information calculating unit 53 separates a resonant magnetic field from the synthetic magnetic field detected by each detecting coil F by using the phase of the driving magnetic field component output from the calibration calculating unit 51, and performs a predetermined calculation process with respect to the separated resonant magnetic field, thereby deriving the current position or direction of the capsule endoscope 10.

As described above, even when the LUT is created in advance and the driving magnetic field component actually generated by the magnetic field generating coil D1 is obtained with reference to the LUT, the resonant magnetic field generated by the capsule endoscope 10 can be accurately separated from the synthetic magnetic field, so that the position of the capsule endoscope 10 can be accurately detected.

In addition, the third modification of the present first embodiment can also be applied to a method of separating a resonant magnetic field from a synthetic magnetic field detected by each detecting coil F based on the phase of a driving magnetic field component and the amplitude of the driving magnetic field component.

In such a case, in the calibration data table creation process, the amplitude is also changed together with the phase and the driving magnetic field output process by the magnetic field generating coil D1 is performed in step S11-3, the amplitude is also calculated together with the phase of the reference voltage value in step S15-3, and the LUT is created in step S19-3, in which the amplitude and the phase of the reference voltage value are made correspond to the reference voltage value.

Furthermore, in the calibration data acquisition process, the calibration calculating unit 51 calculates the amplitude and the phase of the driving current value in step S24-3 similarly to step S24-1 illustrated in FIG. 11, acquires the amplitude and the phase of the driving magnetic field component of each detecting coil F corresponding to the calculated amplitude and phase of the driving current value from the referred LUT in step S27-3, and outputs the acquired each amplitude and phase in step S28-3. In step S3-3, the position information calculating unit 53 performs a position calculation process of obtaining the difference between the synthetic magnetic field detected by the detecting coil F and the driving magnetic field based on the amplitude and the phase of the driving magnetic field component calculated by the calibration calculating unit 51, and calculating the position and direction of the capsule endoscope 10 by using the obtained difference as the resonant magnetic field by the capsule endoscope 10.

Fourth Modification According to First Embodiment

Next, a fourth modification of the first embodiment will be described. In the fourth modification of the first embodiment, since the phase of a driving magnetic field in the magnetic field generating coil D1 is the same as the phase of a driving current flowing through the magnetic field generating coil D1, the calibration calculating unit 51 outputs the phase of a driving current, which is detected by the current detecting unit 32, as the phase of a component of a driving magnetic field at the detection value of a synthetic magnetic field detected by the magnetic field detecting coil F.

A position detection process in the fourth modification of the first embodiment will be described. In the fourth modification of the first embodiment, the calibration calculation process is performed to calculate the phase of the driving magnetic field component of the synthetic magnetic field detected by the detecting coil F illustrated in step S2 of FIG. 4, and then the position calculation process by the position information calculating unit 53 illustrated in step S3 of FIG. 4 and the position detection completion determination process by the control unit 21 illustrated in step S4 of FIG. 4 are performed.

Figure 17:
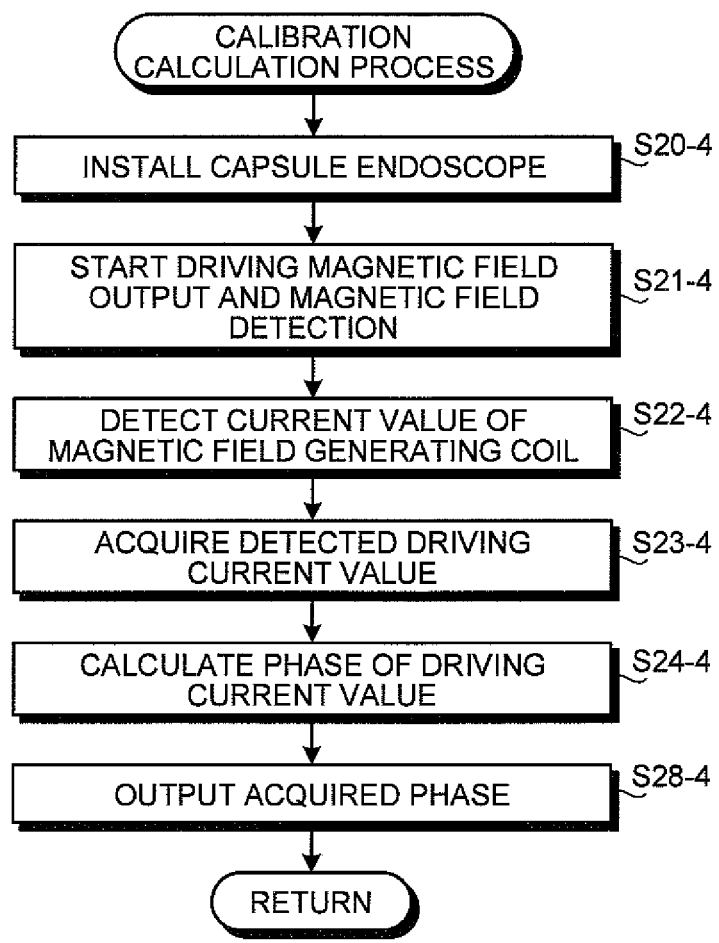
FIG. 17 is a flowchart illustrating the procedure of a calibration calculation process according to a fourth modification of the first embodiment.

Next, the calibration calculation process in the fourth modification of the first embodiment will be described. FIG. 17 is a flowchart illustrating the procedure of the calibration calculation process according to the fourth modification of the first embodiment.

As illustrated in FIG. 17, in the calibration calculation process according to the fourth modification of the first embodiment, similarly to step S20 and step S21 of FIG. 6, in order to start a position detection process, the capsule endoscope 10 (detected object) is installed in the detection space K (step S20-4), and the driving magnetic field output by the magnetic field generating coil D1 and the magnetic field detection by each detecting coil F are started (step S21-4). Then, similarly to step S22 of FIG. 6, the current detecting unit 32 detects the current value of the driving current flowing through the magnetic field generating coil D1, in synchronization with the magnetic field detection of each detecting coil F (step S22-4). Similarly to step S23 of FIG. 6, the driving current value detected by the current detecting unit 32 is acquired in the calibration calculating unit 51 as a driving current value (step S23-4). Next, similarly to step S24 of FIG. 6, the calibration calculating unit 51 calculates the phase of the driving current value (step S24-4). Then, the calibration calculating unit 51 outputs the phase of the driving current, which is detected by the current detecting unit 32, as the phase of the component of the driving magnetic field at the detection value of the synthetic magnetic field detected by the magnetic field detecting coil F (step S28-4). The position information calculating unit 53 separates a resonant magnetic field from the synthetic magnetic field detected by each detecting coil F by using the phase of the driving magnetic field component output from the calibration calculating unit 51, and performs a predetermined calculation process with respect to the separated resonant magnetic field, thereby deriving the current position or direction of the capsule endoscope 10.

Since the phase of the driving magnetic field in the magnetic field generating coil D1 is approximately the same as the phase of the driving current flowing through the magnetic field generating coil D1, even in the fourth modification of the first embodiment, similarly to the first embodiment, it is possible to accurately separate a resonant magnetic field, which is generated by the capsule endoscope 10, from the synthetic magnetic field.

Second Embodiment

Figure 18:
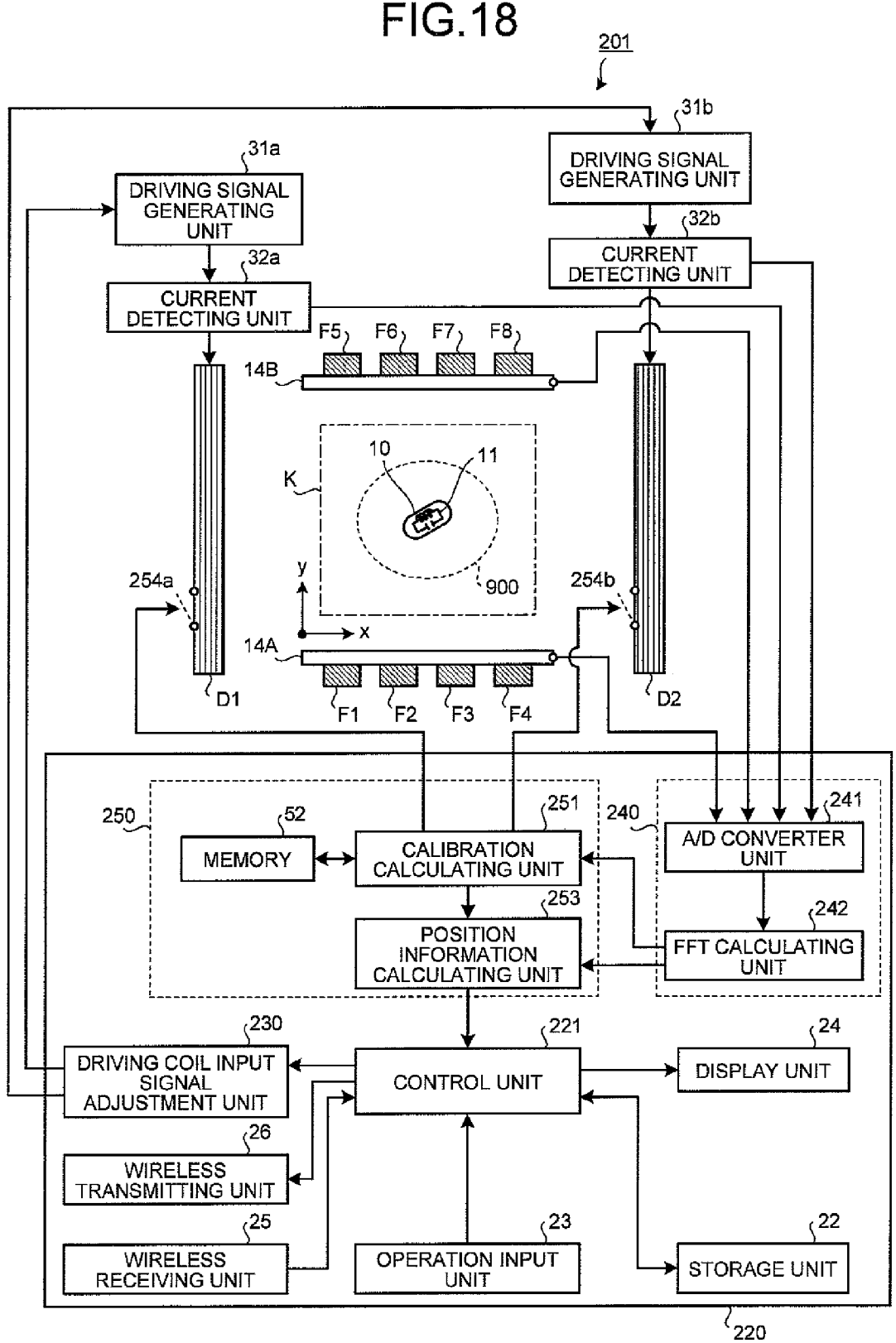
FIG. 18 is a schematic diagram illustrating the schematic configuration of a position detecting system according to a second embodiment.

Next, a second embodiment will be described. FIG. 18 is a schematic diagram illustrating the schematic configuration of a position detecting system 201 according to the second embodiment. As illustrated in FIG. 18, the position detecting system 201 according to the second embodiment includes a plurality of magnetic field generating coils D1 and D2 that generate driving magnetic fields in a detection space K with an approximately uniform distribution, driving signal generating units 31a and 31b, and current detecting units 32a and 32b, wherein the driving signal generating unit 31a and the current detecting unit 32a correspond to the magnetic field generating coil D1, and the driving signal generating unit 31b and the current detecting unit 32b correspond to the magnetic field generating coil D2.

Furthermore, the position detecting system 201 includes an external device 220, instead of the external device 20 illustrated in FIG. 1. The external device 220 includes a control unit 221 instead of the control unit 21 illustrated in FIG. 1, a driving coil input signal adjustment unit 230 instead of the driving coil input signal adjustment unit 30 illustrated in FIG. 1, a converter 240 instead of the converter 40 illustrated in FIG. 1, and a position detecting unit 250 instead of the position detecting unit 50 illustrated in FIG. 1.

The control unit 221 controls each element of the external device 220. The driving coil input signal adjustment unit 230 adjusts the amplitude or phase of a signal used for driving the magnetic field generating coils D1 and D2. The driving signal generating units 31a and 31b generate driving signals, which are input to the magnetic field generating coils D1 and D2, under the control of the driving coil input signal adjustment unit 230, respectively. The converter 240 includes an A/D converter 241 and an FFT calculating unit 242. Similarly to the A/D converter 41, the A/D converter 241 performs A/D conversion with respect to detection signals of a plurality of detecting coils F and the current detecting units 32a and 32b. Similarly to the FFT calculating unit 42, the FFT calculating unit 242 generates FFT data indicating each synthetic magnetic field component detected by each detecting coil F, and the driving current detected by the current detecting units 32a and 32b. The position detecting unit 250 includes a calibration calculating unit 251, a memory 52 for storing a predetermined reference value, and a position information calculating unit 253. The calibration calculating unit 251 calculates the phases of the driving magnetic field components at the detection values of the synthetic magnetic field components detected by the detecting coils F based on the detection values of the driving currents detected by the current detecting units 32a and 32b. The position information calculating unit 253 calculates the position and direction of the capsule endoscope 10 based on detection results detected by the detecting coils F and a calculation result calculated by the calibration calculating unit 251.

Moreover, the magnetic field generating coils D1 and D2 are provided with switches 254a and 254b, respectively. The switch 254a opens a closed loop of a coil of the magnetic field generating coil D1, and the switch 254b opens a closed loop of a coil of the magnetic field generating coil D2. In the case of acquiring reference values of the magnetic field generating coils D1 and D2, the calibration calculating unit 251 allows the switches 254a and 254b to open the closed loops of magnetic field generating coils, other than magnetic field generating coils from which reference values are to be acquired.

In the position detecting system 201 including a plurality of magnetic field generating coils, in the case of acquiring reference values, the closed loops of magnetic field generating coils, other than magnetic field generating coils from which reference values are to be acquired, are opened, so that the influence of interference between the magnetic field generating coils D1 and D2 is eliminated, and a correct reference value is acquired for each magnetic field generating coil.

Figure 19:
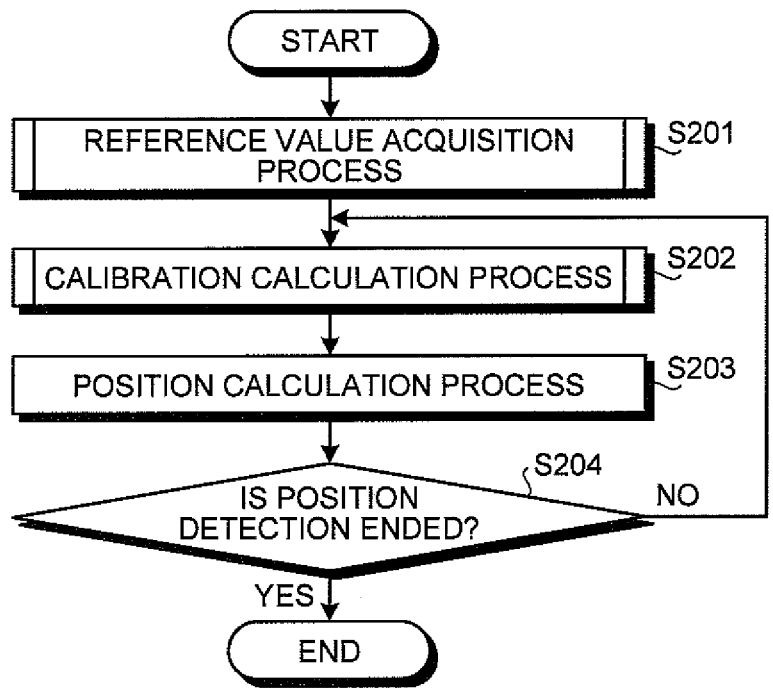
FIG. 19 is a flowchart illustrating the procedure of a position detection process in the position detecting system illustrated in FIG. 18.

Next, a position detection process in the position detecting system 201 will be described. FIG. 19 is a flowchart illustrating the procedure of the position detection process in the position detecting system 201 illustrated in FIG. 18.

As illustrated in FIG. 19, the position detecting system 201 performs a reference value acquisition process of acquiring a detection value of a driving magnetic field detected by each detecting coil F and detection values of driving currents detected by the current detecting units 32a and 32b as reference values in the case in which the capsule endoscope 10 is not positioned in the detection space K (step S201). In step 5201, each reference value is acquired for each magnetic field generating coil. Next, the calibration calculating unit 251 performs a calibration calculation process of calculating the phase of a driving magnetic field component of a synthetic magnetic field detected by each detecting coil F (step S202). Then, the position information calculating unit 253 performs a position calculation process of obtaining a component, which has a phase difference approximately orthogonal to the phase of the driving magnetic field component calculated by the calibration calculating unit 251, from the synthetic magnetic field detected by each detecting coil F, and operating the position and direction of a detected object based on the obtained component (step S203). Thereafter, similarly to step S4 of FIG. 4, a position detection completion determination process by the control unit 221 is performed (step S204). In addition, when it is determined that the position detection process has not been completed (step S204: No), the control unit 221 returns to step S202 in order to continue the position detection, and performs the calibration calculation process. Meanwhile, when it is determined that the position detection process has been completed (step S204: Yes), the control unit 221 also completes a control process for the magnetic field generating coils D1 and D2, the detecting coil F, the converter 240, and the position detecting unit 250, together with the completion of the position detection.

Figure 20:
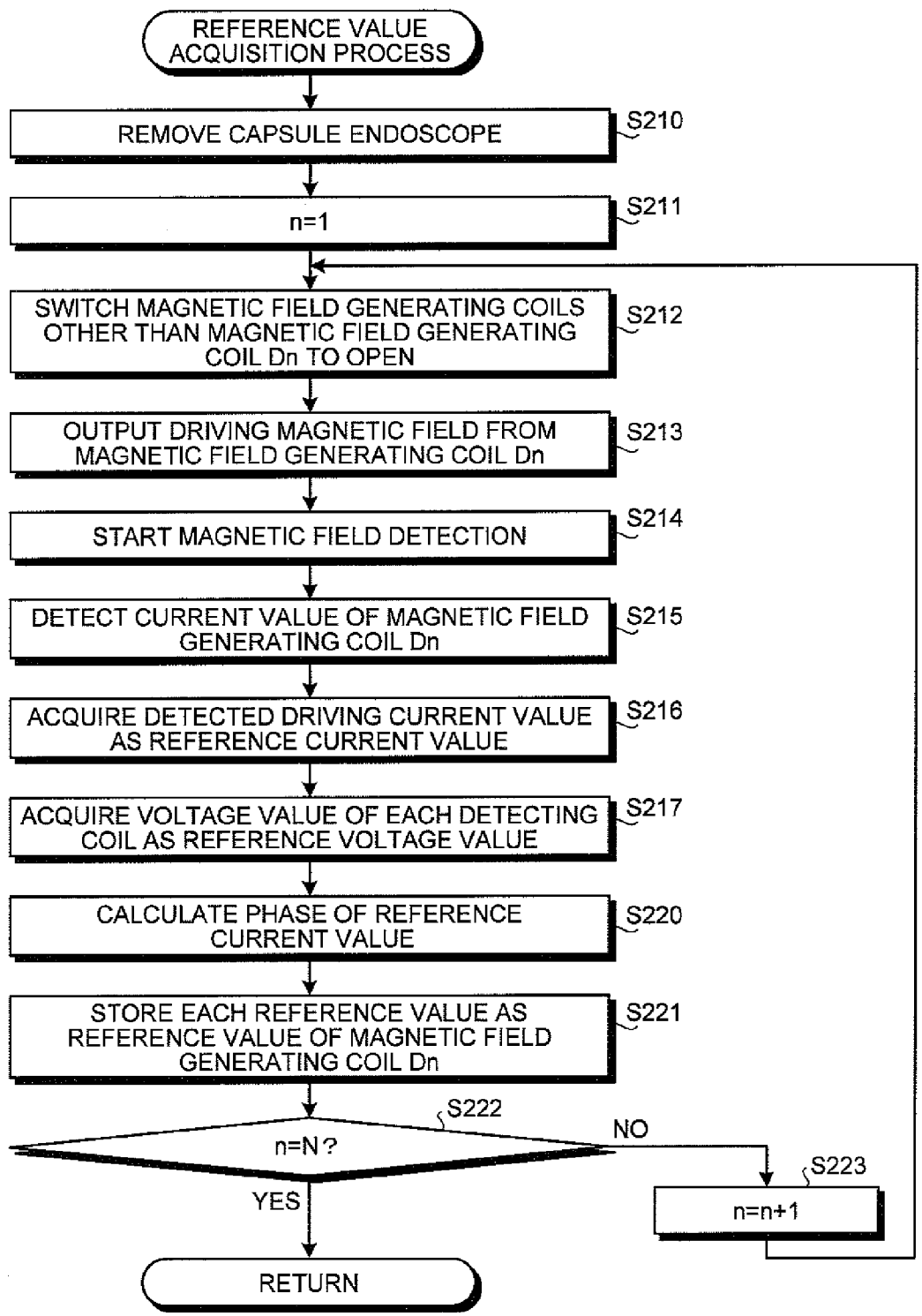
FIG. 20 is a flowchart illustrating the procedure of a reference value acquisition process illustrated in FIG. 19.

Next, the reference value acquisition process illustrated in FIG. 19 will be described. FIG. 20 is a flowchart illustrating the procedure of the reference value acquisition process illustrated in FIG. 19. As illustrated in FIG. 20, the capsule endoscope 10 (detected object) is taken out of the detection space K (step S210). First, in order to acquire a reference value of the magnetic field generating coil D1, the calibration calculating unit 251 initializes an identification number n for identifying the magnetic field generating coils D1 and D2, and sets n=1 (step S211). Then, the calibration calculating unit 251 switches magnetic field generating coils other than a magnetic field generating coil Dn (step S212) to open. In such a case, since the identification number n for identifying the magnetic field generating coils D1 and D2 is 1, the calibration calculating unit 251 controls the switch 254b such that the closed loop of the magnetic field generating coil D2, other than the magnetic field generating coil D1, is opened. As a consequence, a magnetic field formed in the detection space K denotes only a driving magnetic field generated by the magnetic field generating coil D1.

Then, each process is performed to acquire the reference value of the magnetic field generating coil D1. To this end, in the position detecting system 201, a driving magnetic field is output from the magnetic field generating coil D1 (step S213) and magnetic field detection by the detecting coil F is started (step S214). Next, the current detecting unit 32a detects a current value of the driving current flowing through the magnetic field generating coil D1, in synchronization with the magnetic field detection by each detecting coil F (step S215). The driving current value detected by the current detecting unit 32a is acquired in the calibration calculating unit 251 as a reference current value of the magnetic field generating coil D1 after a predetermined frequency component is separated in the converter 240 (step S216). Meanwhile, in the same manner, each voltage value corresponding to the magnetic field detected by each detecting coil F is acquired in the calibration calculating unit 251 as a reference voltage value of each detecting coil F corresponding to the magnetic field generating coil D1 after a predetermined frequency component is separated in the converter 240 (step S217).

Then, the calibration calculating unit 251 calculates the phase of a reference current value corresponding to the magnetic field generating coil D1 based on the acquired reference current value corresponding to the magnetic field generating coil D1 (step S220). The calibration calculating unit 251 stores the reference current value, the reference voltage value, and each reference value of the phase of the reference current value in the memory 52 as reference values corresponding to the magnetic field generating coil D1 (step S221), and completes the reference value acquisition process corresponding to the magnetic field generating coil D1.

Next, the calibration calculating unit 251 compares the identification number n for identifying the magnetic field generating coils D1 and D2 with a maximum value N and determines whether n=N is established (step S222). When it is determined that n is not equal to N (step S222: No), the calibration calculating unit 251 adds 1 to n to establish n=n+1 (step S223), and performs each process to acquire a reference value of the magnetic field generating coil D2. To this end, the procedure returns to steps S212, the calibration calculating unit 251 controls the switch 254a such that the closed loop of the magnetic field generating coil D1, other than the magnetic field generating coil D2, is opened, and allows the magnetic field generated in the detection space K to be only a driving magnetic field generated by the magnetic field generating coil D2. Next, the driving magnetic field is output from the magnetic field generating coil D2 (step S213), processes of step S214 to step S221 are performed to acquire the reference value of the magnetic field generating coil D2. Meanwhile, when it is determined that n=N is established (step S222: Yes), the calibration calculating unit 251 completes the reference value acquisition process.

Figure 21:
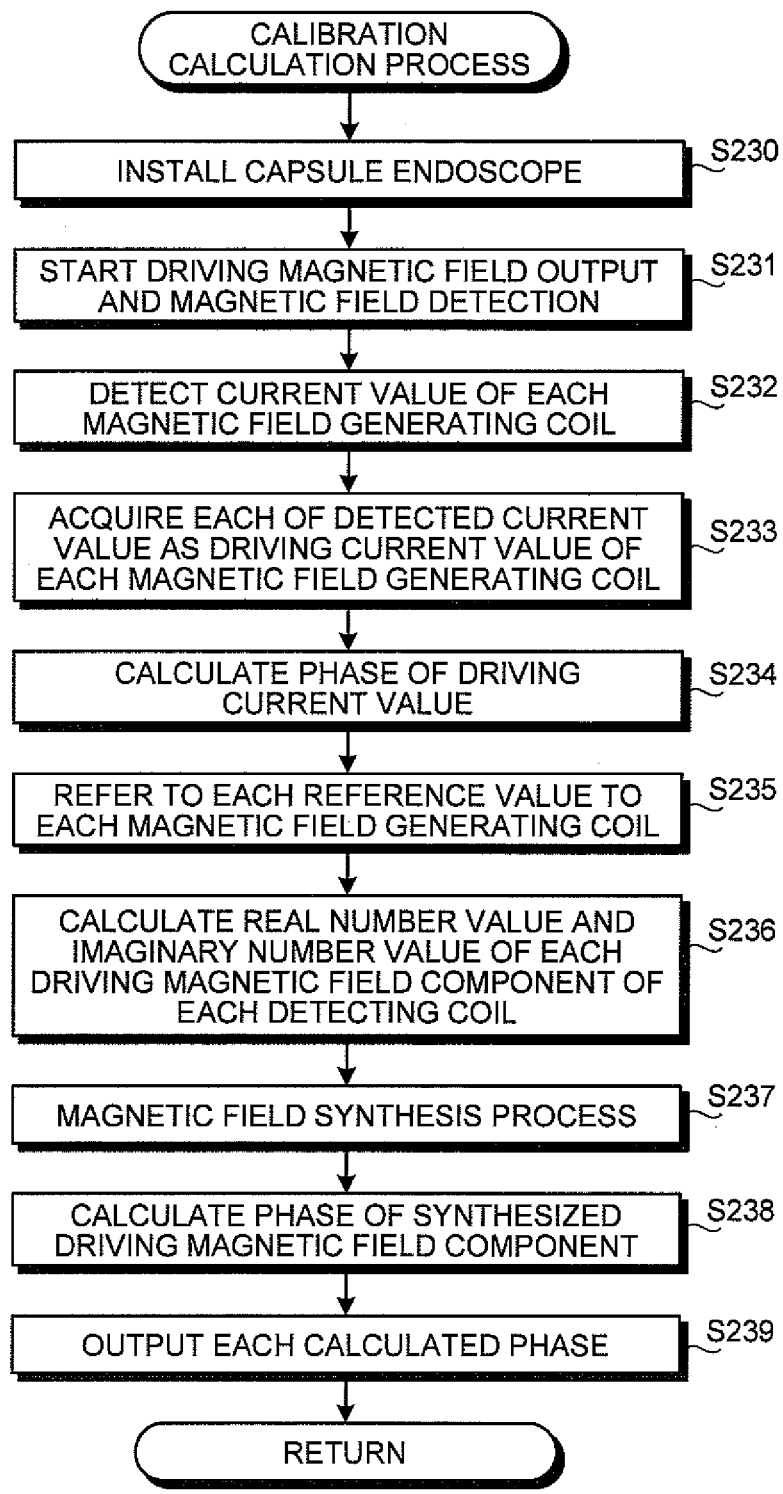
FIG. 21 is a flowchart illustrating the procedure of a calibration calculation process illustrated in FIG. 19.

Next, the calibration calculation process illustrated in FIG. 19 will be described. FIG. 21 is a flowchart illustrating the procedure of the calibration calculation process illustrated in FIG. 19. As illustrated in FIG. 21, in the calibration calculation process, similarly to step S20 of FIG. 6, in order to start a position detection process, the capsule endoscope 10 (detected object) is installed in the detection space K (step S230), and the driving magnetic field output process by the magnetic field generating coils D1 and D2 and the magnetic field detection by the detecting coil F are started (step S231). The voltage value corresponding to the magnetic field detected by each detecting coil F is output to the position information calculating unit 253 as the synthetic magnetic field detected by each detecting coil F after the voltage value is separated to a predetermined frequency component used in the position detection in the converter 240.

Then, the current detecting units 32a and 32b detect the current values of the driving currents flowing through the magnetic field generating coils D1 and D2, in synchronization with the magnetic field detection of each detecting coil F (step S232). Then, each driving current value detected by the current detecting unit 32 is acquired in the calibration calculating unit 251 as driving current values corresponding to the magnetic field generating coils D1 and D2 after a predetermined frequency component is separated in the converter 240 (step S233).

Next, the calibration calculating unit 251 calculates the phases of the driving current values corresponding to the magnetic field generating coils D1 and D2, respectively (step S234). Then, the calibration calculating unit 251 refers to the reference values in the memory 52, which correspond to the magnetic field generating coils D1 and D2, (step S235).

The calibration calculating unit 251 calculates a real number value and an imaginary number value of each driving magnetic field component of the synthetic magnetic field detected by each detecting coil F for each of the magnetic field generating coils D1 and D2 based on the calculated phases of the driving current values and the referred reference values corresponding to the magnetic field generating coils D1 and D2 (step S236). Then, the calibration calculating unit 251 performs a process of synthesizing the driving magnetic field components of the magnetic field generating coils D1 and D2 for each detecting coil F based on the real number value and the imaginary number value of each driving magnetic field component corresponding to each of the magnetic field generating coils D1 and D2 (step S237), thereby calculating the phase of the driving magnetic field component, which has been synthesized in step S237, for each detecting coil (step S238). Thereafter, the calibration calculating unit 251 outputs the calculated phases of driving magnetic field components of the magnetic field generating coils D1 and D2 at the synthetic magnetic field detected by each detecting coil F to the position information calculating unit 253 (step S239).

The position information calculating unit 253 performs a separation process, which separates a resonant magnetic field with a phase difference of 90 degrees relative to the driving magnetic field corresponding to the phase of the driving magnetic field component output from the calibration calculating unit 251, from the synthetic magnetic field, for each detection result by each detecting coil F, and performs a predetermined calculation process with respect to the separated resonant magnetic field, thereby deriving the current position or direction of the capsule endoscope 10.

Next, the calculation processes of step S237 and step S238 will be described using the detecting coil F1 of the detecting coils F as an example. In addition, a phase corresponding to the magnetic field generating coil D1 of the phases of the reference current values stored in the memory 52 is set as Dθ, a phase corresponding to the magnetic field generating coil D2 is set as Dφ, a real number value of the reference voltage value corresponding to the magnetic field generating coil D1 of the reference voltage values in the detecting coil F1 is set as DR1, an imaginary number value thereof is set as DI1, a real number value of the reference voltage value corresponding to the magnetic field generating coil D2 is set as DR2, an imaginary number value thereof is set as DI2, the phase of the driving current value, which corresponds to the magnetic field generating coil D1 and is detected by the current detecting unit 32a, is set as Dθ', and the phase of the driving current value, which corresponds to the magnetic field generating coil D2 and is detected by the current detecting unit 32b, is set as Dφ'.

According to a process corresponding to step S236, first, the calibration calculating unit 251 calculates the phase difference ΔDθ between the reference current value corresponding to the magnetic field generating coil D1 and the driving current value by using Equation (11-1) below.

$$D\theta'-D\theta=\Delta D\theta \qquad (11\text{-}1)$$

Moreover, the calibration calculating unit 251 calculates the phase difference ΔDφ between the reference current value corresponding to the magnetic field generating coil D2 and the driving current value by using Equation (11-2) below.

$$D\phi'-D\phi=\Delta D\phi \qquad (11\text{-}2)$$

Next, the calibration calculating unit 251 calculates a real number value DR1' and an imaginary number value DI1' of a driving voltage value, which corresponds to the driving magnetic field component of the magnetic field generating coil D1 of the synthetic magnetic field, which is detected by the detecting coil F1, by using the phase difference ΔDθ calculated by Equation (11-1) and the reference voltage value corresponding to the magnetic field generating coil D1. Specifically, by means of Equation (12-1) and Equation (13-1) below, the phase of each reference voltage value is added to each value of the reference voltage value, which corresponds to the magnetic field generating coil D1, by ΔDθ, thereby calculating the real number value DR1' and the imaginary number value DI1' of the driving voltage value.

$$DR1'=(DR1\times\cos\Delta\theta-DI1\times\sin\Delta\theta) \qquad (12\text{-}1)$$

$$DI1'=(DR1\times\sin\Delta\theta+DI1\times\cos\Delta\theta) \qquad (13\text{-}1)$$

In the same manner, the calibration calculating unit 251 calculates a real number value DR2' and an imaginary number value DI2' of a driving voltage value, which corresponds to the driving magnetic field component of the magnetic field generating coil D2 of the synthetic magnetic field, which is detected by the detecting coil F1, by using the phase difference ΔDφ calculated by Equation (11-2) and the reference voltage value corresponding to the magnetic field generating coil D2. Specifically, by means of Equation (12-2) and Equation (13-2) below, the phase of each reference voltage value is added to each value of the reference voltage value, which corresponds to the magnetic field generating coil D2, by ΔDφ, thereby calculating the real number value DR2' and the imaginary number value DI2' of the driving voltage value.

$$DR2'=(DR2\times\cos\Delta\phi-DI2\times\sin\Delta\phi) \qquad (12\text{-}2)$$

$$DI2'=(DR2\times\sin\Delta\phi+DI2\times\cos\Delta\phi) \qquad (13\text{-}2)$$

Then, according to a process corresponding to step S237, by means of the real number values DR1' and DR2' and the imaginary number values DI1' and DI2' of the driving magnetic field components corresponding to the magnetic field generating coils D1 and D2, which are calculated by Equation (12-1), Equation (12-2), Equation (13-1) and Equation (13-2), and Equation (14-1) and Equation (14-2) below, a real number value SR1 and an imaginary number value SI1 of a driving voltage value, which is obtained by synthesizing the driving magnetic field components of the magnetic field generating coils D1 and D2, are calculated.

$$SR1=DR1'+DR2' \qquad (14\text{-}1)$$

$$SI1=DI1'+DI2' \qquad (14\text{-}2)$$

Then, the calibration calculating unit 251 employs a magnetic field, which is obtained by synthesizing the driving magnetic field components of the magnetic field generating coils D1 and D2, as a driving magnetic field component in the detecting coil F1, and calculates the phase of the driving voltage value in the detecting coil F1 based on the real number value SR2' and the imaginary number value SI2' of the driving voltage value corresponding to the driving magnetic field component. In the same manner, for the detecting coils F2 to F8, the calibration calculating unit 251 calculates the phase of each driving voltage value in the detecting coils F2 to F8.

The position detecting system 201 performs the procedures illustrated in FIGS. 19 to 21, thereby eliminating the influence of interference between the magnetic field generating coils D1 and D2 and acquiring a correct reference value for each of the magnetic field generating coils D1 and D2. Moreover, the position detecting system 201 obtains the phases of the driving magnetic field components, which are actually generated by the magnetic field generating coils D1 and D2, based on the reference values corresponding to the magnetic field generating coils D1 and D2, and the driving current values detected by the current detecting units 32a and 32b, and accurately separates the resonant magnetic field generated by the capsule endoscope 10 from the synthetic magnetic field, thereby accurately detecting the position of the capsule endoscope 10.

First Modification According to Second Embodiment

Next, a first modification of the second embodiment will be described. In the first modification of the second embodiment, the case will be described in which the amplitude as well as the phase of a driving voltage value corresponding to a driving magnetic field component is obtained as a driving magnetic field component, and a resonant magnetic field is separated by subtracting the driving magnetic field component from a synthetic magnetic field.

Figure 22:
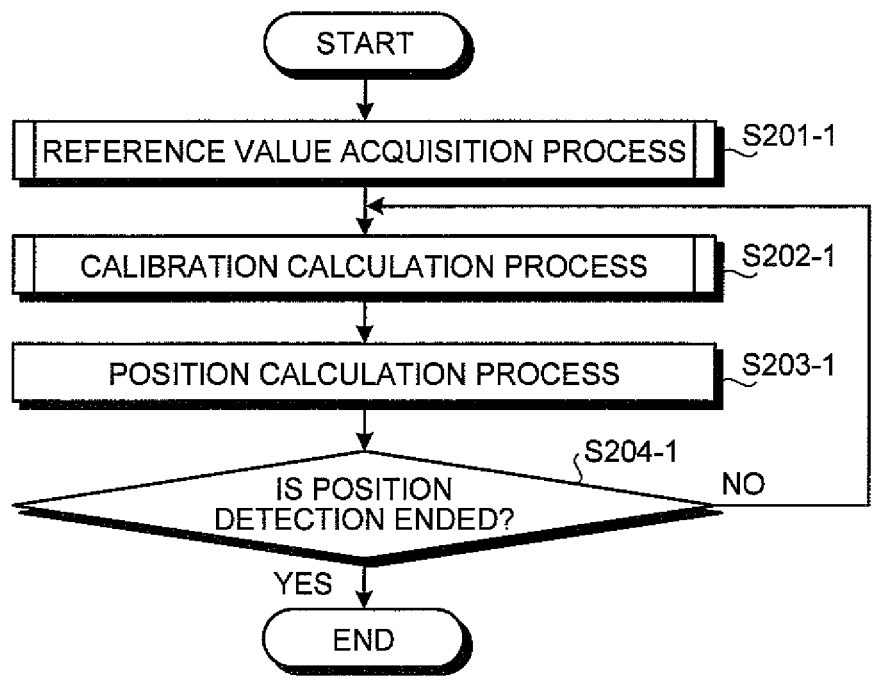
FIG. 22 is a flowchart illustrating the procedure of a position detection process according to a first modification of the second embodiment.

A position detection process in the first modification of the present second embodiment will be described. FIG. 22 is a flowchart illustrating the procedure of the position detection process according to the first modification of the present second embodiment. As illustrated in FIG. 22, in the first modification of the second embodiment, a reference value acquisition process is performed to acquire a detection value of the driving magnetic field detected by each detecting coil F and detection values of driving currents detected by the current detecting units 32a and 32b as reference values in the case in which the capsule endoscope 10 is not positioned in the detection space K (step S201-1). In step S201-1, each reference value is acquired for each magnetic field generating coil. Next, the calibration calculating unit 251 performs a calibration calculation process of calculating the amplitude and the phase of a driving magnetic field component of a synthetic magnetic field detected by each detecting coil F (step S202-1). Then, the position information calculating unit 253 performs a position calculation process of obtaining a difference between the synthetic magnetic field and the driving magnetic field detected by the detecting coil F from the synthetic magnetic field detected by each detecting coil F based on the amplitude and the phase of the driving magnetic field component calculated by the calibration calculating unit 251, and operating the position and direction of the capsule endoscope 10 by employing the obtained difference as the resonant magnetic field generated by the capsule endoscope 10 (step S203-1). Thereafter, similarly to step S4 of FIG. 4, a position detection completion determination process by the control unit 221 is performed (step S204-1). In addition, when it is determined that the position detection process has not been completed (step S204-1: No), the control unit 221 returns to step S202-1 in order to continue the position detection, and performs the calibration calculation process. Meanwhile, when it is determined that the position detection process has been completed (step S204-1: Yes), the control unit 221 also completes a control process for the magnetic field generating coils D1 and D2, the detecting coil F, the converter 240, and the position detecting unit 250, together with the completion of the position detection.

Figure 23:
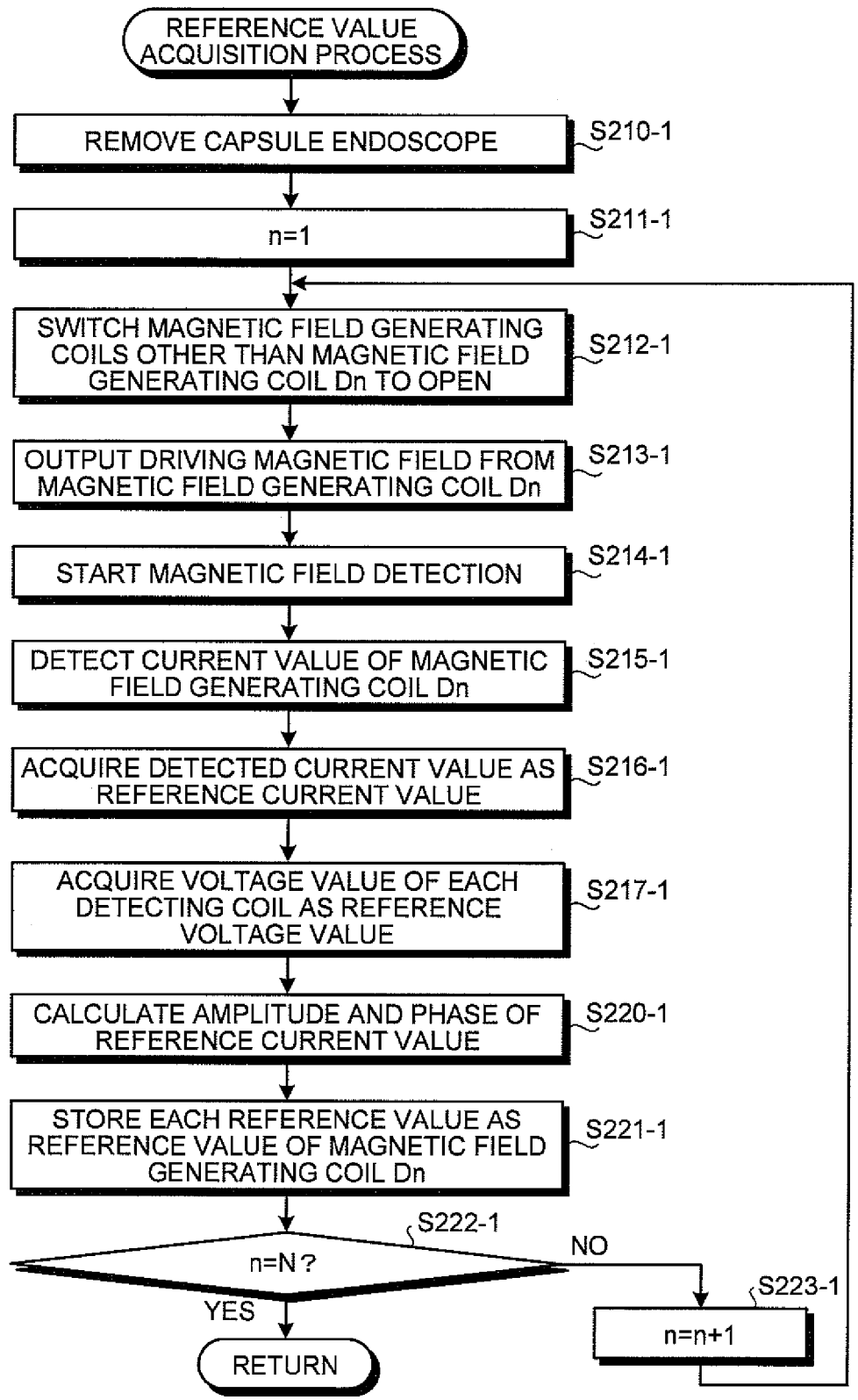
FIG. 23 is a flowchart illustrating the procedure of a reference value acquisition process illustrated in FIG. 22.

Next, the reference value acquisition process illustrated in FIG. 22 will be described. FIG. 23 is a flowchart illustrating the procedure of the reference value acquisition process illustrated in FIG. 22. As illustrated in FIG. 23, the capsule endoscope 10 (detected object) is taken out of the detection space K (step S210-1). Next, in order to acquire a reference value of the magnetic field generating coil D1, similarly to step S211 of FIG. 20, the calibration calculating unit 251 initializes an identification number n and sets n to 1 (step S211-1), and switches magnetic field generating coils other than a magnetic field generating coil Dn to open (step S212-1). The calibration calculating unit 251 controls the switch 254b such that the closed loop of the magnetic field generating coil D2, other than the magnetic field generating coil D1, is opened.

Then, each process is performed to acquire the reference value of the magnetic field generating coil D1. To this end, similarly to step S213 to step S216 illustrated in FIG. 20, in the position detecting system 201, a driving magnetic field is output from the magnetic field generating coil D1 (step S213-1), magnetic field detection by the detecting coil F is started (step S214-1), detection of the driving current value of the magnetic field generating coil D1 by the current detecting unit 32a is performed (step S215-1), and acquisition of the reference current value of the magnetic field generating coil D1 by the calibration calculating unit 251 is performed (step S216-1). Next, similarly to step S217 of FIG. 20, the calibration calculating unit 251 acquires each reference voltage value of each detecting coil F corresponding to the magnetic field generating coil D1 (step S217-1).

Then, the calibration calculating unit 251 calculates the amplitude and the phase of the reference current value corresponding to the magnetic field generating coil D1 based on a real number value and an imaginary number value of the acquired reference current value corresponding to the magnetic field generating coil D1 (step S220-1). The calibration calculating unit 251 stores the reference current value, the reference voltage value, and each reference value of the amplitude and the phase of the calculated reference current value in the memory 52 as reference values corresponding to the magnetic field generating coil D1 (step S221-1), and completes the acquisition of the reference value corresponding to the magnetic field generating coil D1.

Next, similarly to step S222 illustrated in FIG. 20, the calibration calculating unit 251 determines whether n=N is established (step S222-1). When it is determined that n=N is not established (step S222-1: No), the calibration calculating unit 251 adds 1 to n to establish n=n+1 (step S223-1). In order to acquire a reference value of the magnetic field generating coil D2, the procedure returns to steps S212-1, and the calibration calculating unit 251 controls the switch 254a such that the closed loop of the magnetic field generating coil D1, other than the magnetic field generating coil D2, is opened, and performs the processes of step S213-1 to step S221-1. In this way, the reference value of the magnetic field generating coil D2 is acquired. Meanwhile, when it is determined that n=N is established (step S222-1: Yes), the calibration calculating unit 251 completes the reference value acquisition process.

Figure 24:
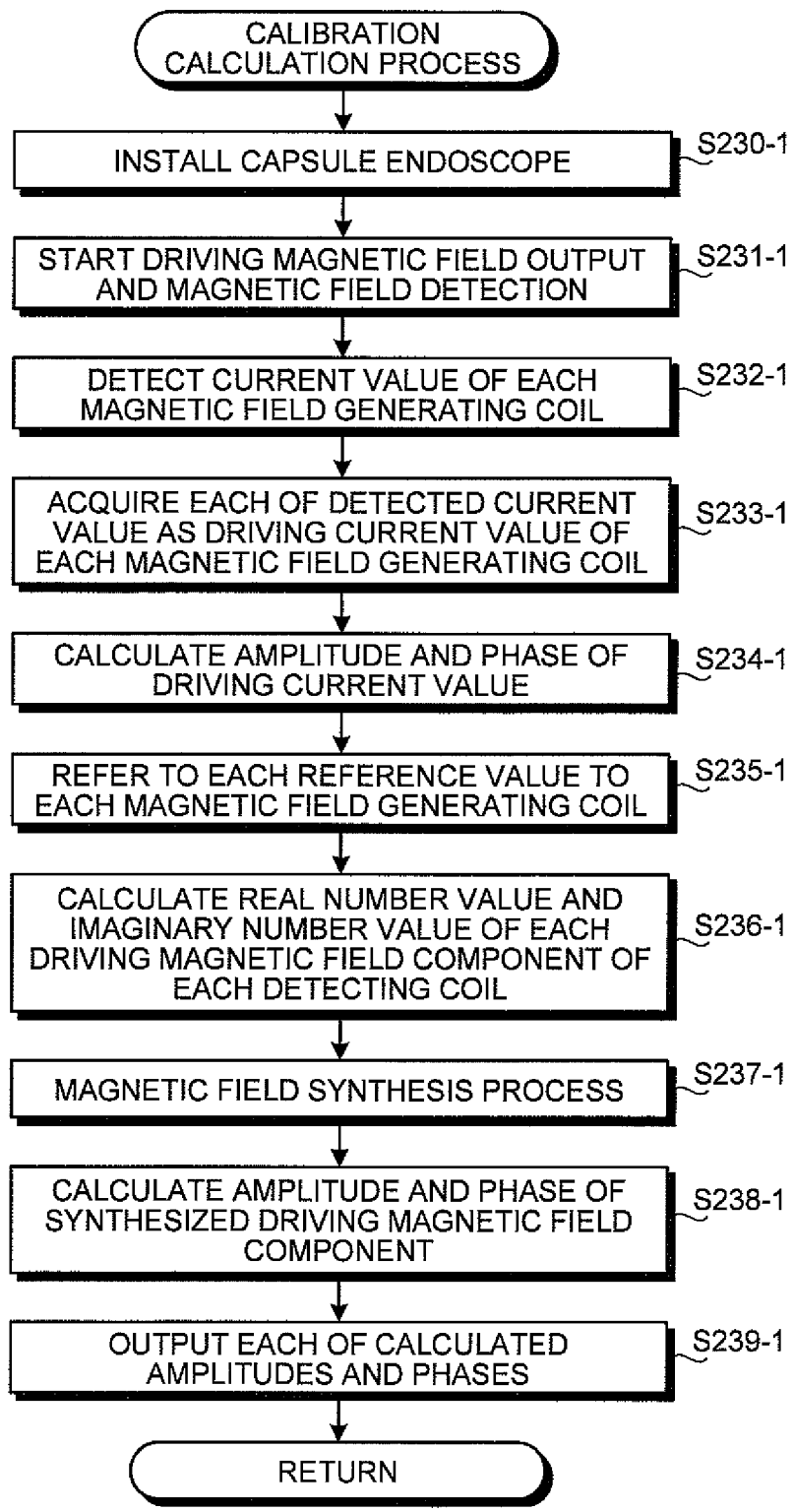
FIG. 24 is a flowchart illustrating the procedure of a calibration calculation process illustrated in FIG. 22.

Next, the calibration calculation process illustrated in FIG. 22 will be described. FIG. 24 is a flowchart illustrating the procedure of the calibration calculation process illustrated in FIG. 22. As illustrated in FIG. 24, in the calibration calculation process, similarly to step S20 of FIG. 6, in order to start a position detection process, the capsule endoscope 10 (detected object) is installed in the detection space K (step S230-1), and the driving magnetic field output process by the magnetic field generating coils D1 and D2 and the magnetic field detection by the detecting coil F are started (step S231-1).

Then, the current detecting units 32a and 32b detect the current values of the driving currents flowing through the magnetic field generating coils D1 and D2, in synchronization with the magnetic field detection of each detecting coil F (step S232-1). The detected current values are acquired in the calibration calculating unit 251 as driving current values corresponding to the magnetic field generating coils D1 and D2 (step S233-1).

Next, the calibration calculating unit 251 calculates the amplitudes and phases of the driving current values corresponding to the magnetic field generating coils D1 and D2, respectively (step S234-1). Then, the calibration calculating unit 251 refers to the reference values in the memory 52, which correspond to the magnetic field generating coils D1 and D2, (step S235-1).

The calibration calculating unit 251 calculates a real number value and an imaginary number value of each driving magnetic field component of the synthetic magnetic field detected by each detecting coil F for each of the magnetic field generating coils D1 and D2 based on the calculated amplitudes and phases of the driving current values and the referred reference values corresponding to the magnetic field generating coils D1 and D2 (step S236-1). Then, the calibration calculating unit 251 performs a process of synthesizing the driving magnetic field components of the magnetic field generating coils D1 and D2 for each detecting coil F based on the real number value and the imaginary number value of each driving magnetic field component corresponding to each of the magnetic field generating coils D1 and D2 (step S237-1), thereby calculating the amplitude and the phase of the driving magnetic field component, which has been synthesized in step S237-1, for each detecting coil (step S238-1). Thereafter, the calibration calculating unit 251 outputs the calculated amplitudes and phases of driving magnetic field components of the magnetic field generating coils D1 and D2 at the synthetic magnetic field detected by each detecting coil F to the position information calculating unit 253 (step S239-1). The position information calculating unit 253 performs a separation process, which separates a resonant magnetic field by subtracting a driving magnetic field corresponding to the amplitude and the phase of the driving magnetic field component output from the calibration calculating unit 251, from the synthetic magnetic field, for each detection result by each detecting coil F, and performs a predetermined calculation process with respect to the separated resonant magnetic field, thereby deriving the current position or direction of the capsule endoscope 10.

Next, the calculation processes of step S237-1 and step S238-1 will be described using the detecting coil F1 of the detecting coils F as an example. In addition, a phase corresponding to the magnetic field generating coil D1 of the phases of the reference current values stored in the memory 52 is set as $D\theta$, a phase corresponding to the magnetic field generating coil D2 is set as $D\phi$, an amplitude corresponding to the magnetic field generating coil D1 of the amplitudes of the reference current values is set as DX, an amplitude corresponding to the magnetic field generating coil D2 is set as DY, a real number value of the reference voltage value corresponding to the magnetic field generating coil D1 of the reference voltage values in the detecting coil F1 is set as DR1, an imaginary number value thereof is set as DI1, a real number value of the reference voltage value corresponding to the magnetic field generating coil D2 is set as DR2, an imaginary number value thereof is set as DI2, the phase of the driving current value, which corresponds to the magnetic field generating coil D1 and is detected by the current detecting unit 32a, is set as $D\theta'$, the amplitude thereof is set as DX', the phase of the driving current value, which corresponds to the magnetic field generating coil D2 and is detected by the current detecting unit 32b, is set as $D\phi'$, and the amplitude thereof is set as DY'.

According to a process corresponding to step S236-1, first, similarly to the second embodiment, the calibration calculating unit 251 calculates the phase difference $\Delta D\theta$ between the reference current value corresponding to the magnetic field generating coil D1 and the driving current value, and the phase difference $\Delta D\phi$ between the reference current value corresponding to the magnetic field generating coil D2 and the driving current value by using Equation (11-1) and Equation (11-2) above.

Next, the calibration calculating unit 251 calculates the ratio Kx of the amplitude of the reference current value corresponding to the magnetic field generating coil D1 and the amplitude of the driving current value by using Equation (15-1) below. Then, the calibration calculating unit 251 calculates the ratio Ky of the amplitude of the reference current value corresponding to the magnetic field generating coil D2 and the amplitude of the driving current value by using Equation (15-2) below.

$$DX'/DX=Kx \tag{15-1}$$

$$DY'/DY=Ky \tag{15-2}$$

Next, the calibration calculating unit 251 calculates a real number value DR1' and an imaginary number value DI1' of a driving voltage value, which corresponds to the driving magnetic field component of the magnetic field generating coil D1 of the synthetic magnetic field detected by the detecting coil F1, by using the phase difference $\Delta D\theta$ calculated by Equation (11-1), the amplitude ratio Kx calculated by Equation (15-1), and the reference voltage value corresponding to the magnetic field generating coil D1. Specifically, by means of Equation (16-1) and Equation (17-1) below, the phase of each reference voltage value is added to each value of the reference voltage value, which corresponds to the magnetic field generating coil D1, by $\Delta D\theta$, and is multiplied by the amplitude ratio Kx, thereby calculating the real number value DR1' and the imaginary number value DI1' of the driving voltage value.

$$DR1'=Kx\times(DR1\times\cos\Delta\theta-DI1\times\sin\Delta\theta) \tag{16-1}$$

$$DI1'=Kx\times(DR1\times\sin\Delta\theta+DI1\times\cos\Delta\theta) \tag{17-1}$$

In the same manner, the calibration calculating unit 251 calculates a real number value DR2' and an imaginary number value DI2' of a driving voltage value, which corresponds to the driving magnetic field component of the magnetic field generating coil D2 of the synthetic magnetic field detected by the detecting coil F1, by using the phase difference $\Delta D\phi$ calculated by Equation (11-2), the amplitude ratio Ky calculated by Equation (15-2), and the reference voltage value corresponding to the magnetic field generating coil D2. Specifically, by means of Equation (16-2) and Equation (17-2) below, the phase of each reference voltage value is added to each value of the reference voltage value, which corresponds to the magnetic field generating coil D1, by $\Delta D\phi$, and is multiplied by the amplitude ratio Ky, thereby calculating the real number value DR2' and the imaginary number value DI2' of the driving voltage value.

$$DR2'=Ky\times(DR2\times\cos\Delta\phi-DI2\times\sin\Delta\phi) \tag{16-2}$$

$$DI2'=Ky\times(DR2\times\sin\Delta\phi+DI2\times\cos\Delta\phi) \tag{17-2}$$

Then, according to a process corresponding to step S237-1, by means of the real number values DR1' and DR2' and the imaginary number values DI1' and DI2' of the driving magnetic field components corresponding to the magnetic field generating coils D1 and D2, which are calculated by Equation (16-1), Equation (16-2), Equation (17-1), and Equation (17-2), and Equation (18-1) and Equation (18-2) below, a real number value SR1 and an imaginary number value SI1 of a driving voltage value, which is obtained by synthesizing the driving magnetic field components of the magnetic field generating coils D1 and D2, are calculated.

$$SR1=DR1'+DR2' \tag{18-1}$$

$$SI1=DI1'+DI2' \tag{18-2}$$

Then, the calibration calculating unit 251 employs a magnetic field, which is obtained by synthesizing the driving magnetic field components of the magnetic field generating coils D1 and D2, as a driving magnetic field component in the detecting coil F1, and calculates the amplitude and the phase of the driving voltage value in the detecting coil F1 based on the real number value SR2' and the imaginary number value SI2' of the driving voltage value corresponding to the driving magnetic field component. In the same manner, for the detecting coils F2 to F8, the calibration calculating unit 251 calculates the amplitude and the phase of each driving voltage value in the detecting coils F2 to F8.

The position detecting system 201 performs the procedures illustrated in FIGS. 22 to 24, thereby eliminating the influence of interference between the magnetic field generating coils D1 and D2 and acquiring a correct reference value for each of the magnetic field generating coils D1 and D2, resulting in the achievement of the same effect as the second embodiment.

In addition, the second modification of the first embodiment and the third modification of the first embodiment as described above can be applied to the second embodiment and the first modification of the second embodiment, respectively. That is, in the second embodiment and the first modification of the second embodiment, by means of the characteristics of the magnetic field generating coils D1 and D2 prepared in advance, the characteristics of each magnetic field detecting coil F, and relative position relation between the magnetic field generating coils D1 and D2 and the detecting coil F, a real number value and an imaginary number value of a driving magnetic field component may also be calculated for each of the magnetic field generating coils D1 and D2 through simulation. Furthermore, in the second embodiment and the first modification of the second embodiment, an LUT (look-up table), in which detection values (driving magnetic fields by the magnetic field generating coils D1 and D2) of detecting coils are made correspond to detection values of the current detecting units 32a and 32b, may be created in advance for each of the magnetic field generating coils D1 and D2, and a real number value and an imaginary number value of a driving magnetic field component may also be calculated for each of the magnetic field generating coils D1 and D2 at the time of position detection with reference to each of the LUT.

Figure 25:
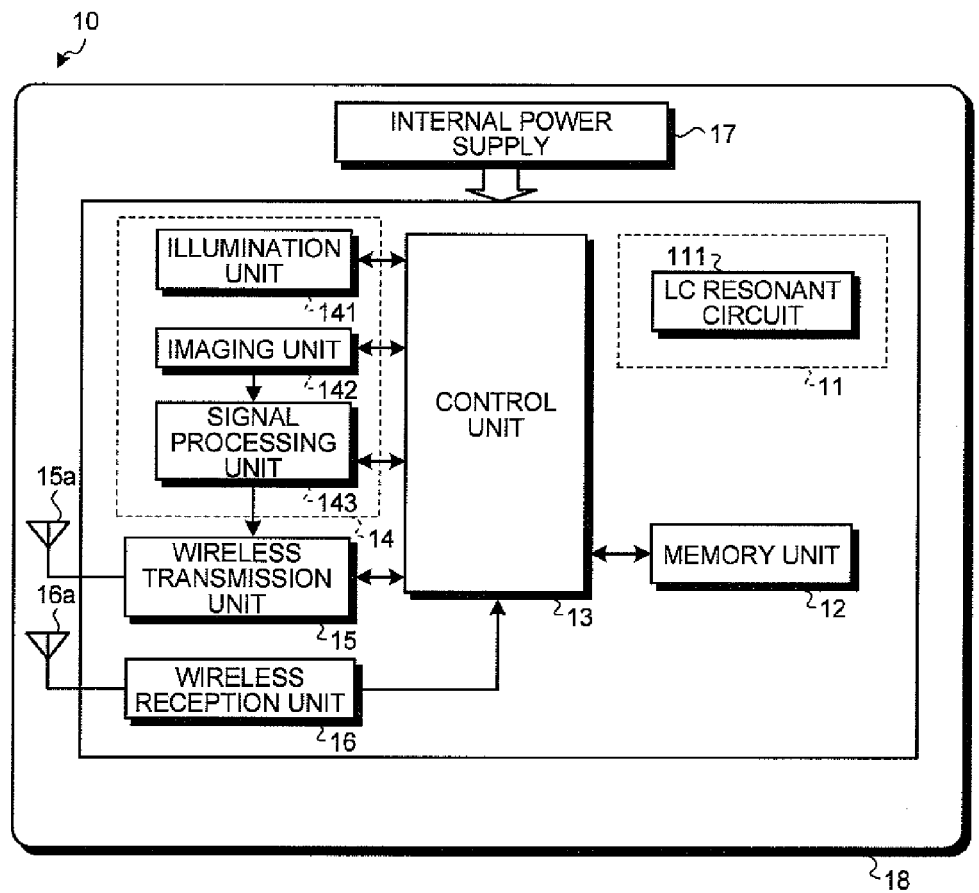
FIG. 25 is a block diagram illustrating the schematic configuration example of a capsule endoscope according to the first or the second embodiment.

Hereinafter, the capsule endoscope 10 illustrated in FIG. 1 will be described. As illustrated in FIG. 25, the capsule endoscope 10, for example, includes a resonant magnetic field generating unit 11, a memory unit 12, a control unit 13, an in-vivo information acquisition unit 14, a wireless transmitting unit 15 and a transmitting antenna 15a, a wireless receiving unit 16 and a receiving antenna 16a, and an internal power supply 17. The resonant magnetic field generating unit 11 includes an LC resonant circuit 111 having a capacitor (C) and an inductor (L) connected in parallel to each other. The control unit 13 controls each element of the capsule endoscope 10. The in-vivo information acquisition unit 14 acquires various pieces of information in the subject 900. The wireless transmitting unit 15 and a transmitting antenna 15a transmit in-vivo information acquired by the in-vivo information acquisition unit 14 to an exterior of the capsule endoscope 10 as a wireless signal. The wireless receiving unit 16 and a receiving antenna 16a receive various operation instructions and the like transmitted from an external device 20 as a wireless signal. The internal power supply 17 supplies power to each element of the capsule endoscope 10. FIG. 25 is a block diagram illustrating the schematic configuration example of the capsule endoscope 10 according to the present embodiment.

The in-vivo information acquisition unit 14, for example, includes an imaging unit 142, an illumination unit 141, and a signal processing unit 143. The imaging unit 142 acquires an in-vivo image as the in-vivo information. The illumination unit 141 illuminates an interior of the subject 900 when the imaging unit 142 captures an image of the interior of the subject 900. The signal processing unit 143 performs predetermined signal processing with respect to the in-vivo image acquired by the imaging unit 142.

Figure 26:
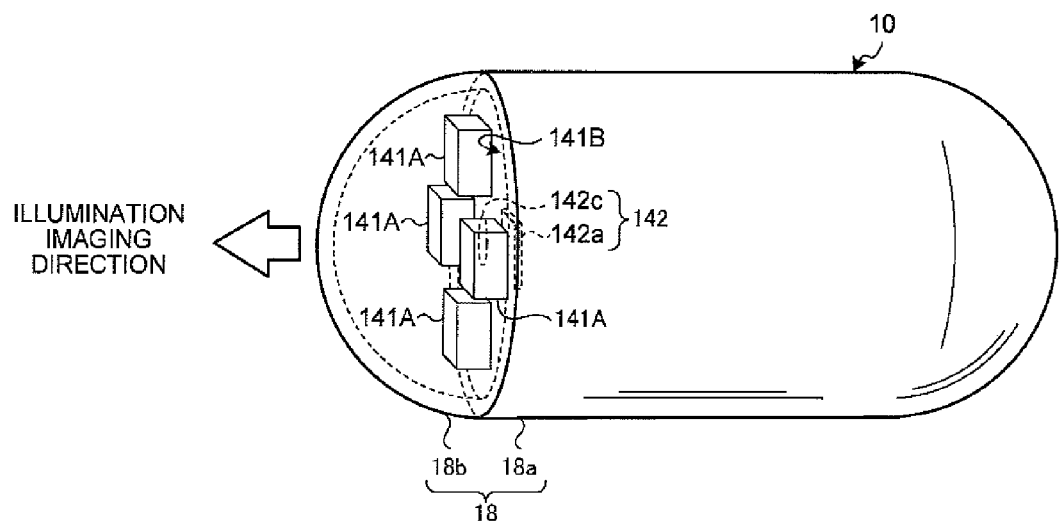
FIG. 26 is an external appearance diagram illustrating the schematic configuration example of a capsule endoscope according to the first or the second embodiment of the present invention.

As illustrated in FIG. 26, the imaging unit 142, for example, includes an imaging element 142a, an objective lens 142c, and an imaging element driving circuit (not illustrated). The imaging element 142a converts an incident light into an electrical signal to form an image. The objective lens 142c disposed at a light receiving surface side of the imaging element 142a. The imaging element driving circuit drives the imaging element 142a. FIG. 26 is an external appearance diagram illustrating the schematic configuration example of the capsule endoscope 10 according to present embodiment.

As illustrated in FIG. 26, the imaging element 142a, for example, may use a CCD camera, a CMOS camera, and the like. The imaging element driving circuit drives the imaging element 142a to acquire an in-vivo image of an analog signal under the control of the control unit 13. Then, the imaging element driving circuit outputs the in-vivo image of an analog signal, which is read from the imaging element 142a, to the signal processing unit 143.

Furthermore, as illustrated in FIG. 26, the illumination unit 141 includes a plurality of light sources 141A, and a light source driving circuit for driving the light sources 141A. Each light source 141A, for example, may use an LED (Light Emitting Diode) and the like. The light source driving circuit drives the light sources 141A according to the driving of the imaging unit 142 under the control of the control unit 13, thereby illuminating the interior of the subject 900.

Returning again to FIG. 25, the signal processing unit 143, for example, performs predetermined signal processing, such as sampling, amplification or A/D (Analog-to-Digital) conversion, with respect to the analog in-vivo image which is input from the imaging unit 142, thereby generating a digital in-vivo image. The in-vivo image having suffered from various processes is input to the wireless transmitting unit 15.

In addition, the in-vivo information acquisition unit 14 may also include a sensor element (not illustrated) and a sensor element driving circuit for controlling the driving of the sensor element. The sensor element, for example, includes a thermometer, a manometer, a pH meter and the like, and appropriately acquires the temperature, pressure, a pH value and the like of the interior of the subject 900 as the in-vivo information. The sensor element driving circuit drives the sensor element to acquire the in-vivo information, and inputs the in-vivo information to the wireless transmitting unit 15 under the control of the control unit 13.

The wireless transmitting unit 15 is connected to the transmitting antenna 15a including a coil antenna and the like, performs various processes, such as superposition, modulation and up-conversion to a reference frequency signal for transmission, with respect to the in-vivo information, such as the in-vivo image, which is input from the signal processing unit 143, and transmits a resultant signal to the external device 20 from the transmitting antenna 15a as a wireless signal.

The wireless receiving unit 16 is connected to the receiving antenna 16a including a coil antenna and the like, receives various operation instructions and the like, which are transmitted from the external device 20 as a wireless signal via the receiving antenna 16a, performs various processes, such as filtering, down-conversion, demodulation and decoding, with respect to a received signal, and outputs a resultant signal to the control unit 13.

The control unit 13, for example, includes a CPU, an MPU and the like, and reads and executes a program and a parameter from a storage unit (not illustrated) based on various operation instructions and the like, which are input from the external device 20 via the wireless receiving unit 16, thereby controlling each element of the capsule endoscope 10.

The memory unit 12, for example, includes an RAM, an ROM and the like, and holds a program and a parameter executed when the control unit 13 controls each element. The memory unit 12 appropriately stores the in-vivo information such as the in-vivo image acquired by the in-vivo information acquisition unit 14.

The internal power supply 17, for example, includes a button battery, which is a primary battery or a secondary battery, and a power source circuit, which boosts power output from the button battery and supplies a boosted power to each element of the capsule endoscope 10, and supplies driving power to each element of the capsule endoscope 10. However, the present invention is not limited to the button battery.

Furthermore, the above-mentioned units (11, 13, 14, 15, 15a, 16, 16a and 17), for example, are received in a capsule-type casing 18. For example, as illustrated in FIG. 26, the casing 18 includes a receptacle 18a having an approximately cylindrical shape or a semielliptical shape, and a cap 18b. One end of the receptacle 18a has a hemispheric dome shape and the other end of the receptacle 18a is opened. The cap 18b having a semispherical shape is fitted around the opening of the receptacle 18a to seal the casing 18. The casing 18, for example, has a size to an extent that the casing 18 can be swallowed by the subject 900. Furthermore, in the present embodiment, at least the cap 18b is made of a transparent material. The above-mentioned light source 141A is mounted on a circuit board 141B having the above-mentioned light source driving circuit (not illustrated). In the same manner, the imaging element 142a and the objective lens 142c are mounted on a circuit board (not illustrated) having the imaging element driving circuit (not illustrated). The circuit board 141B having the light source 141A and the circuit board having the imaging element 142a are disposed to the side of the transparent cap 18b in the casing 18. At this time, an element mounting surface of each circuit board is directed to the side of the transparent cap 18b. Thus, the imaging/illumination direction of the imaging element 142a and the light source 141A is directed to the exterior of the capsule endoscope 10 via the transparent cap 18b as illustrated in FIG. 26.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detecting system comprising:
    a detected object disposed in a detection space to generate an induced magnetic field in response to a driving magnetic field generated in the detection space;
    one or more magnetic field generating coils that generate the driving magnetic field in the detection space;
    a magnetic field detecting coil that detects a synthetic magnetic field of the driving magnetic field and the induced magnetic field generated by the detected object in response to the driving magnetic field;
    a current detecting unit that detects a driving current flowing through the magnetic field generating coil in synchronization with magnetic field detection by the magnetic field detecting coil;
    a position information calculating unit that calculates a position and a direction of the detected object based on a detection value of the synthetic magnetic field detected by the magnetic field detecting coil and a detection value of the driving current detected by the current detecting unit; and
    a calibration calculating unit that calculates a phase of a driving magnetic field component which corresponds to the driving magnetic field at the detection value of the synthetic magnetic field detected by the magnetic field detecting coil, based on the detection value of the driving current detected by the current detecting unit,
    wherein the position information calculating unit obtains a component having a phase difference approximately orthogonal to the phase of the driving magnetic field component calculated by the calibration calculating unit, from the synthetic magnetic field detected by the magnetic field detecting coil, and calculates the position and direction of the detected object based on the obtained component.

2. The position detecting system according to claim 1, further comprising a storage unit that stores the detection value of the magnetic field detected by the magnetic field detecting coil and the detection value of the driving current detected by the current detecting unit when the detected object is not positioned in the detection space, as a reference value,
    wherein the calibration calculating unit calculates the phase of the driving magnetic field component based on the detection value of the driving current detected by the current detecting unit and the reference value stored in the storage unit.

3. The position detecting system according to claim 2, wherein the calibration calculating unit calculates the phase of the driving magnetic field component by using a phase difference between the detection value of the driving current stored in the storage unit as the reference value and the detection value of the driving current detected by the current detecting unit.

4. The position detecting system according to claim 2, wherein the magnetic field generating coil includes a plurality of magnetic field generating coils, and
    the position detecting system comprises:
    a switching unit that opens a closed loop of each of the magnetic field generating coils; and
    a switching controller that, when the referenced value is acquired, allows the switching unit to open a closed loop of the magnetic field generating coil other than the magnetic field generating coil from which the referenced value is to be acquired.

5. The position detecting system according to claim 1, wherein the calibration calculating unit calculates the phase of the driving magnetic field component at the detection value of the synthetic magnetic field detected by the magnetic field detecting coil, based on characteristics of the magnetic field generating coil, characteristics of the magnetic field detecting coil, relative position information between the magnetic field generating coil and the magnetic field detecting coil, and the detection value of the driving current detected by the current detecting unit.

6. The position detecting system according to claim 1, further comprising a storage unit that stores a correspondence relation in which each detection value of a magnetic field detected by the magnetic field detecting coil is made correspond to each detection value of the driving current detected by the current detecting unit, when the magnetic field generating coil generates a driving magnetic field with a different phase,
    wherein the calibration calculating unit calculates the phase of the driving magnetic field component corresponding to the driving magnetic field based on the detection value of the driving current detected by the current detecting unit and the correspondence relation stored in the storage unit.

7. The position detecting system according to claim 1, wherein the calibration calculating unit calculates a phase of the driving current based on the detection value of the driving current detected by the current detecting unit, and outputs the calculated phase as a phase of a component of the driving magnetic field at the detection value of the synthetic magnetic field detected by the magnetic field detecting coil.

8. A position detecting system comprising:
a detected object disposed in a detection space to generate an induced magnetic field in response to a driving magnetic field generated in the detection space;
one or more magnetic field generating coils that generate the driving magnetic field in the detection space;
a magnetic field detecting coil that detects a synthetic magnetic field of the driving magnetic field and the induced magnetic field generated by the detected object in response to the driving magnetic field;
a current detecting unit that detects a driving current flowing through the magnetic field generating coil in synchronization with magnetic field detection by the magnetic field detecting coil;
a position information calculating unit that calculates a position and a direction of the detected object based on a detection value of the synthetic magnetic field detected by the magnetic field detecting coil, and a detection value of the driving current detected by the current detecting unit; and
a calibration calculating unit that calculates an amplitude and a phase of a driving magnetic field component, which corresponds to the driving magnetic field at the detection value of the synthetic magnetic field detected by the magnetic field detecting coil, based on the detection value of the driving current detected by the current detecting unit,
wherein the position information calculating unit obtains a difference between the synthetic magnetic field detected by the magnetic field detecting coil and the driving magnetic field based on the amplitude and the phase of the driving magnetic field component calculated by the calibration calculating unit, and calculates the position and direction of the detected object based on the obtained difference.

9. The position detecting system according to claim 8, further comprising a storage unit that stores the detection value of the magnetic field detected by the magnetic field detecting coil and the detection value of the driving current detected by the current detecting unit when the detected object is not positioned in the detection space, as a reference value,
wherein the calibration calculating unit calculates the amplitude and the phase of the driving magnetic field component based on the detection value of the driving current detected by the current detecting unit and the reference value stored in the storage unit.

10. The position detecting system according to claim 9, wherein the calibration calculating unit calculates the amplitude and the phase of the driving magnetic field component by using an amplitude ratio and a phase difference between the detection value of the driving current stored in the storage unit as the reference value and the detection value of the driving current detected by the current detecting unit.

11. The position detecting system according to claim 9, wherein the magnetic field generating coil includes a plurality of magnetic field generating coils, and
the position detecting system comprises:
a switching unit that opens a closed loop of each of the magnetic field generating coils; and
a switching controller that, when the referenced value is acquired, allows the switching unit to open a closed loop of the magnetic field generating coil other than the magnetic field generating coil from which the referenced value is to be acquired.

12. The position detecting system according to claim 8, wherein the calibration calculating unit calculates the amplitude and the phase of the driving magnetic field component at the detection value of the synthetic magnetic field, which is detected by the magnetic field detecting coil, based on characteristics of the magnetic field generating coil, characteristics of the magnetic field detecting coil, relative position information between the magnetic field generating coil and the magnetic field detecting coil, and the detection value of the driving current detected by the current detecting unit.

13. The position detecting system according to claim 8, further comprising a storage unit that stores a correspondence relation in which each detection value of a magnetic field detected by the magnetic field detecting coil is made correspond to each detection value of the driving current detected by the current detecting unit, when the magnetic field generating coil generates a driving magnetic field with different amplitude and phase,
wherein the calibration calculating unit calculates the amplitude and the phase of the driving magnetic field component based on the detection value of the driving current detected by the current detecting unit and the correspondence relation stored in the storage unit.

14. A position detecting system operating method for detecting a position of a detected object which is introduced into a detection space including at least one magnetic field generating coil for generating a driving magnetic field and generates an induced magnetic field in response to the driving magnetic field, the method comprising:
a magnetic field detecting step of detecting, by the magnetic field detecting coil, a synthetic magnetic field of the driving magnetic field and the induced magnetic field generated by the detected object in response to the driving magnetic field;
a current detecting step of detecting, by a current detecting unit, a driving current flowing through the magnetic field generating coil in synchronization with detection of the synthetic magnetic field;
a calibration calculating step of calculating, by a calibration calculating unit, a phase of a driving magnetic field component corresponding to the driving magnetic field at a detection value of the synthetic magnetic field, based on a detection value of the driving current; and
a position information calculating step of calculating, by a position information calculating unit, a position and a direction of the detected object based on the detection value of the synthetic magnetic field and the phase of the driving magnetic field component,
wherein the position information calculating step includes calculating, using the synthetic magnetic field detected at the magnetic field detecting step, a component having a phase difference approximately orthogonal to the phase of the driving magnetic field component calculated at the calibration calculating step and then calculating the position and direction of the detected object based on the calculated component.

15. A position detecting system operating method for detecting a position of a detected object which is introduced into a detection space including at least one magnetic field generating coil for generating a driving magnetic field and generates an induced magnetic field in response to the driving magnetic field, the method comprising:
a magnetic field detecting step of detecting, by the magnetic field detecting coil, a synthetic magnetic field of the driving magnetic field and the induced magnetic field generated by the detected object in response to the driving magnetic field;

a current detecting step of detecting, by a current detecting unit, a driving current flowing through the magnetic field generating coil in synchronization with detection of the synthetic magnetic field;

a calibration calculating step of calculating, by a calibration calculating unit, an amplitude and a phase of a driving magnetic field component corresponding to the driving magnetic field at a detection value of the synthetic magnetic field, based on a detection value of the driving current; and a position information calculating step of calculating, by a position information calculating unit, a position and a direction of the detected object based on the detection value of the synthetic magnetic field and the amplitude and the phase of the driving magnetic field component, wherein the position information calculating step includes calculating, based on the amplitude and the phrase of the driving magnetic field component calculated at the calibration calculating step, a difference between the synthetic magnetic field detected at the magnetic field detecting step and the driving magnetic field and then calculating the position and direction of the detected object based on the calculated difference.

* * * * *